United States Patent
Lowther et al.

(10) Patent No.: US 9,267,149 B2
(45) Date of Patent: *Feb. 23, 2016

(54) TRANSGENIC ALOE PLANTS FOR PRODUCTION OF PROTEINS AND RELATED METHODS

(71) Applicant: TheGreenCell, Inc., Miami, FL (US)

(72) Inventors: William J. Lowther, Washington, DC (US); Wen-Shuz Yeow, Bethesda, MD (US); Kevin Lorick, Kensington, MD (US); Marisol Pages, Santo Domingo (DO); Nicola J. Lowther, Washington, DC (US)

(73) Assignee: TheGreenCell, Inc., Silver Spring, MD (US)

( * ) Notice: Subject to any disclaimer, the term of this patent is extended or adjusted under 35 U.S.C. 154(b) by 351 days.

This patent is subject to a terminal disclaimer.

(21) Appl. No.: 13/663,992

(22) Filed: Oct. 30, 2012

(65) Prior Publication Data

US 2013/0061353 A1  Mar. 7, 2013

Related U.S. Application Data

(62) Division of application No. 13/188,815, filed on Jul. 22, 2011, now Pat. No. 8,816,154, which is a division of application No. 11/528,056, filed on Sep. 26, 2006, now Pat. No. 8,008,546.

(60) Provisional application No. 60/720,540, filed on Sep. 26, 2005.

(51) Int. Cl.
*C12N 15/82* (2006.01)
*A01H 5/00* (2006.01)

(52) U.S. Cl.
CPC .................................. *C12N 15/8257* (2013.01)

(58) Field of Classification Search
None
See application file for complete search history.

(56) References Cited

U.S. PATENT DOCUMENTS

| | | | | |
|---|---|---|---|---|
| 5,939,288 | A * | 8/1999 | Thornburg | 435/69.8 |
| 6,365,807 | B1 | 4/2002 | Christou et al. | |
| 6,448,046 | B1 * | 9/2002 | Donson et al. | 435/70.1 |
| 6,627,182 | B2 | 9/2003 | Bailey | |
| 8,008,546 | B2 * | 8/2011 | Lowther et al. | 800/298 |
| 8,816,154 | B2 * | 8/2014 | Lowther et al. | 800/288 |
| 2003/0059486 | A1 | 3/2003 | Bailey | |

FOREIGN PATENT DOCUMENTS

| | | |
|---|---|---|
| CN | 1315999 A | 10/2001 |
| CN | 1742565 A | 3/2006 |
| EP | 0 598 589 B1 | 4/2004 |
| WO | WO 00/11175 | 3/2000 |
| WO | WO 01/07613 A2 | 2/2001 |
| WO | WO 01/55433 | 8/2001 |
| WO | WO 02/38780 A | 5/2002 |

OTHER PUBLICATIONS

Chen et al. Expression of bioactive human interferon-gamma in transgenic rice cell suspension cultures. (2004) Transgenic Research; vol. 13, pp. 499-551.*
Carter et al. A comparison of DNA cleavage by the restriciton enzymes SaIPI and PstI. (1980) Nucleic Acids Research; vol. 8; pp. 4943-4954.*
Vazquez et al. Antiinflammatory activity of extracts from Aloe vera gel. (1996) J. of Ethnopharmacology; vol. 55; pp. 69-75.*
Office Action for corresponding Chinese application No. 2012100713885 issued on Jul. 29, 2013 and English translation thereof.
Decision to Grant for corresponding Japanese application No. 2008-532506 issued on Jul. 30, 2013 and English translation thereof.
Geetha et al., "In vitro Plant Regeneration from Different Seedling Explants of Blackgram [*Vigna mungo* (L.) Hepper] via Organogenesis," Breeding Science (1997) vol. 47; 311-315.
Notice of Rejection Grounds for corresponding Japanese Patent Application No. 2012-126986 mailed on Feb. 4, 2014.
Sato, T. "Basic Studies of Organ and Callus Culture in Woody Plants," Bulletin of Forestry and Forest Products Research Institute (1991) No. 360; 35-119.
Venkatachalam et al., "In Vitro Callus Culture and Plant Regeneration from Different Explants of Groundnut (*Arachis hypogaea* L.)," Breeding Science (1996) vol. 4; 315-320.
Sinnott R A; "Agricultural Biotechnology: Genetic Engineering of Sunflower and Aloe with Virulent Strains of Agrobacterium." Arizona State University Press, Dec. 1995, 148 pgs (Pg count includes Cover sheet, Abstract, Table of Contents and Article).
Zhang, Linna, et al. Activation of a mouse macrophage cell line by acemannan: The major carbohydrate fraction from Aloe vera gel. Immunopharmacology, 1996, 35(2), pp. 119-128.
Chen, T-L, et at. Expression of bioactive human interferon-gamma in transgenic rice cell suspension cultures. Transgenic Research, 2004, 13, pp. 499-510.

(Continued)

*Primary Examiner* — Cathy Kingdon Worley
(74) *Attorney, Agent, or Firm* — Billion & Armitage; Patti J. Jurkovich

(57) ABSTRACT

The present inventions provide transgenic aloe plants and recombinant constructs for transforming aloe plants, aspects of which, may be applied to other monocots. The recombinant constructs may include one or more DNA sequences encoding mammalian proteins and at least one promoter capable of directing the expression of recombinant proteins in an aloe plant. The present inventions also provide methods for constructing and reproducing a transgenic aloe plant. The present inventions include methods for transfection of an aloe plant with several genes of interest simultaneously. The aloe plant production methods of the inventions may provide the potential to inexpensively and more safely mass-produce some biologically active compounds including biopharmaceuticals for disease therapy, diagnosis and prevention, and is more accessible to the less affluent countries. The aloe plant production methods may also produce proteins for cosmetics.

11 Claims, 12 Drawing Sheets

(56) References Cited

OTHER PUBLICATIONS

Hansen, G, Recent Advances in the Transformation of Plants. Trends in Plant Science—Reviews, Jun. 1999, vol. 4 No. 6, pp. 226-231.
Australian Examination and Search Report for related Australian Patent Application Serial No. 2006292072 filed Sep. 26, 2006.
Japanese Examination Report for related Japanese Patent Application Serial No. 2008-532506 filed Sep. 26, 2006.
International Search Report and Written Opinion for Related PCT Patent Application WO2007/035966 published Mar. 29, 2007.
International Preliminary Report on Patentability for Related PCT Patent Application WO2007/035966 published Mar. 29, 2007.

* cited by examiner

Figure 5

The Ubiquitin promoter sequence

```
TGATCCCCTAATGAGCATTGCATGTCTAAGTTATAAAAAATTACCACATATTTTTTGTCACACTTGTTGAAGTGC
AGTTTATCTATCTTTATACATATATTTAAACTTCACTCTACGAATAATATAATCTATAGTACTACAATAATCAGTG
TTTTAGAGAATCATATAAATGAACAGTTAGACATGGTCTAAAGGACAATTGAGTACTTTGACAACAGGACTCTACA
GTTTATCTCTTAGTGTGCATGTGTTCTCCTTTTTTTGCAAATAGCTTCACCTATATAATACTTCATCCATTTTA
TTAGTACATCCATTTAGGGTTAAGGTTTATAGACTAATTTTTTAGTACATCTATTTATTCTATTT
```
Sall
```
AGCCTCTAAATTAAGAAAACTAAAACTCTATTTTAGTTTTTTTATTAATTTAATAATTAGAATATAAAATAGAATAAAATAAA
GTGACTAAAAATTAAACAAATACCCTTAAGAAATTAAAAAACTAAGGAAACATTTTCTGTTTCGAGTAGATAA
TGCCAGCCTGTTAAACGCCGTCGACGAGTCTAAGGACACCAGGGAACCAGCAGCGTGCGGTCGGGCCA
AGCGAAGCAGACGGCACGGCATCTCTGTCGCTCTCTGGGCCCCTCTGGAGAGTTCCGCTCCACCGTTGGAC
TGCTCGGCTGTCGGCATCCAGAAATTGCGTGGCGAGACGTGAGCCCGGCACGGCAGGCGGGCCTCC
TCCTCCTCTCACGGCACCGGCAGCTACGGGGATTCCTTTCCCACCGCTCCTTCGCTTCCCTTCCTCGCCCGC
```
TATA box
```
CGTAATAAATAGACACCCCCTCCACACCCTCTTTCCCCAACCTCGTGTTGTTCGGAGCGCACACACAACC
```
Bglll
```
AGATCTCCCCCAAATCCACCCGTCGGCACCTTCGCTTCAAG
```
Xbal
```
GTACGCCGCTCGTCCTCCCCCCCCTCTCCTCTACCTTCTCTAGATCGGGCCGTTCCGGTCCATGGTTAGGGCCCG
GTAGTTCTACTTCTCGTTCATGTTTGTGTAGATCCGTGTTTGTGATAGATCCGTGCTGCTAGCGTTCGTACACGG
ATGCGACCTGTACGTTCAGACACGTTCTGATTGCTAACTTGCCAGTGTTCTCTTGGGGAATCCTGGGATGGCTC
TAGCCGTTCCGCAGACGGATCGATTTCATGATTTTTTTTGTTCGTTGCATAGGGTTTGGTTTGCCCTTTCCT
TTATTTCAATATATGCCGTGCACTGTTTGTCGGGTCATCTTTTCATGTTTTTTTTGGCTTGGTGTTGTGATGATGT
```
Xbal
```
GGTCTGGTGGGCGGTCGTTCTAGATCGGAGTAGAATTCTGTTTCAAACTACCTGGTGATTATTAATTTTGGA
TCTGTATGTGTGCCATACATATTCATAGTTACGAATTGAAGATGATGGAAATATCGATCTAGGATAGGTA
TACATGTTGATGCGGGTTTCATTCATCGTTCTAGATCGGAGTAGAATACTGTTCAAACTAACTGGTGGATTTATTAATTTTGG
```
Xbal
```
GTTGGGCGGTCGTTCATTCATCGTTCTAGATCGGAGTAGAATACTGTTCAAACTAACTGGTGGATTTATTAATTTTGG
ATCTGTATGTGTGCCATACATCTTCATAGTTACGAGTTAAGATGATGGAAGTATCGATCTAGGATAGGT
ATACATGTTGATGTGGGTTTACTGATGCATATACATGATGGCATATGCAGCATCTATTCATAGTCTAACCTTG
AGTACCTATCTATTATAAACAAGTATGTTTATAATTATTTGATCTTGATATACTGGATGATGCATATGCAG
CAGCTATATGTGGATTTTTTAGCCCTGCCTTCATACGCTATTTATTTGCTTGGTACTGTTCTTTGTCGATGCTC
```
Pstl
```
ACCCTGTTGTTTGGTGTTACTTCTGCAG
```

MAR region

Primer R for MAR
Xhol

5' UTR
Transcription Initiation

1st Intron
EcoRI

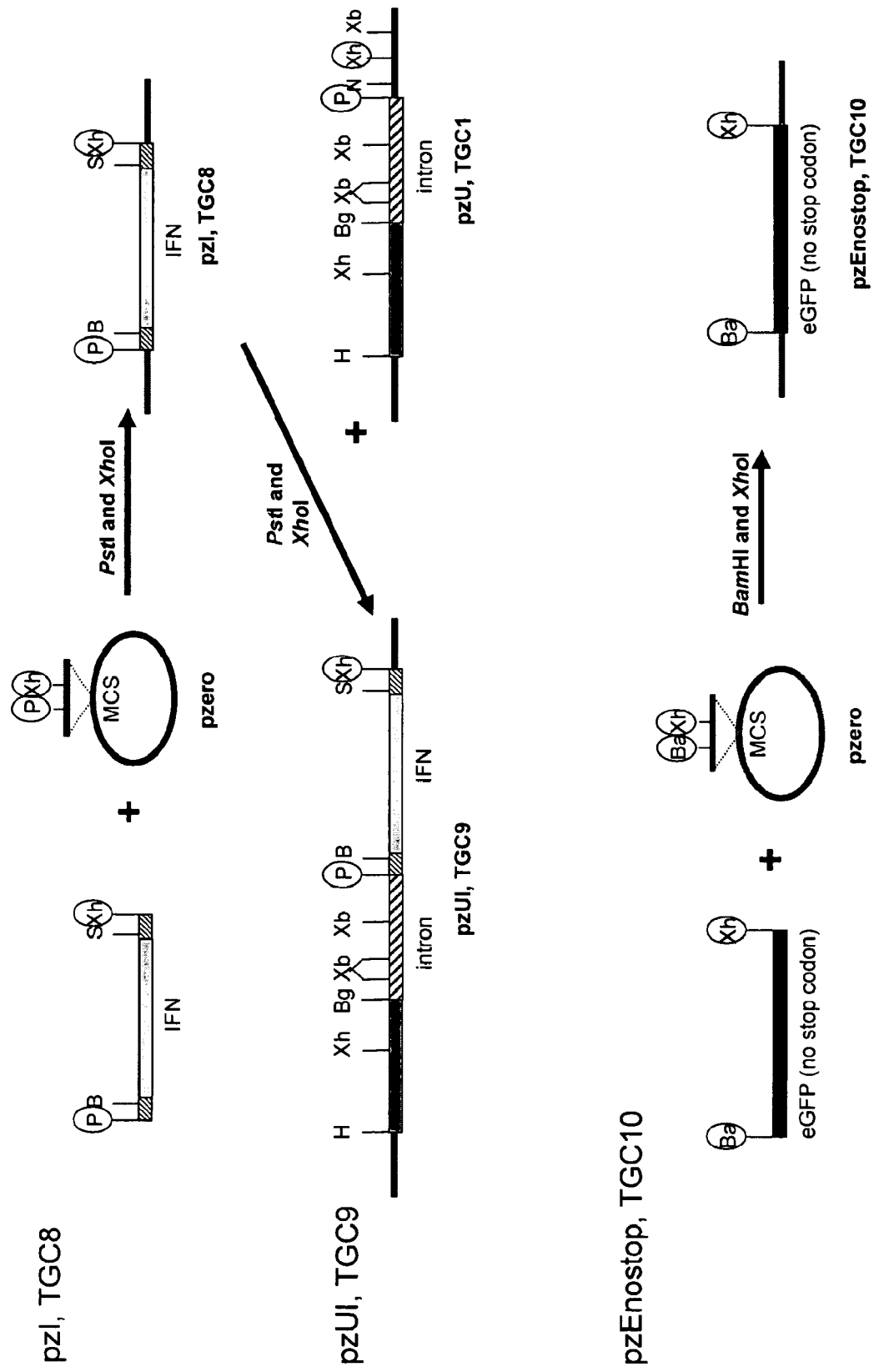

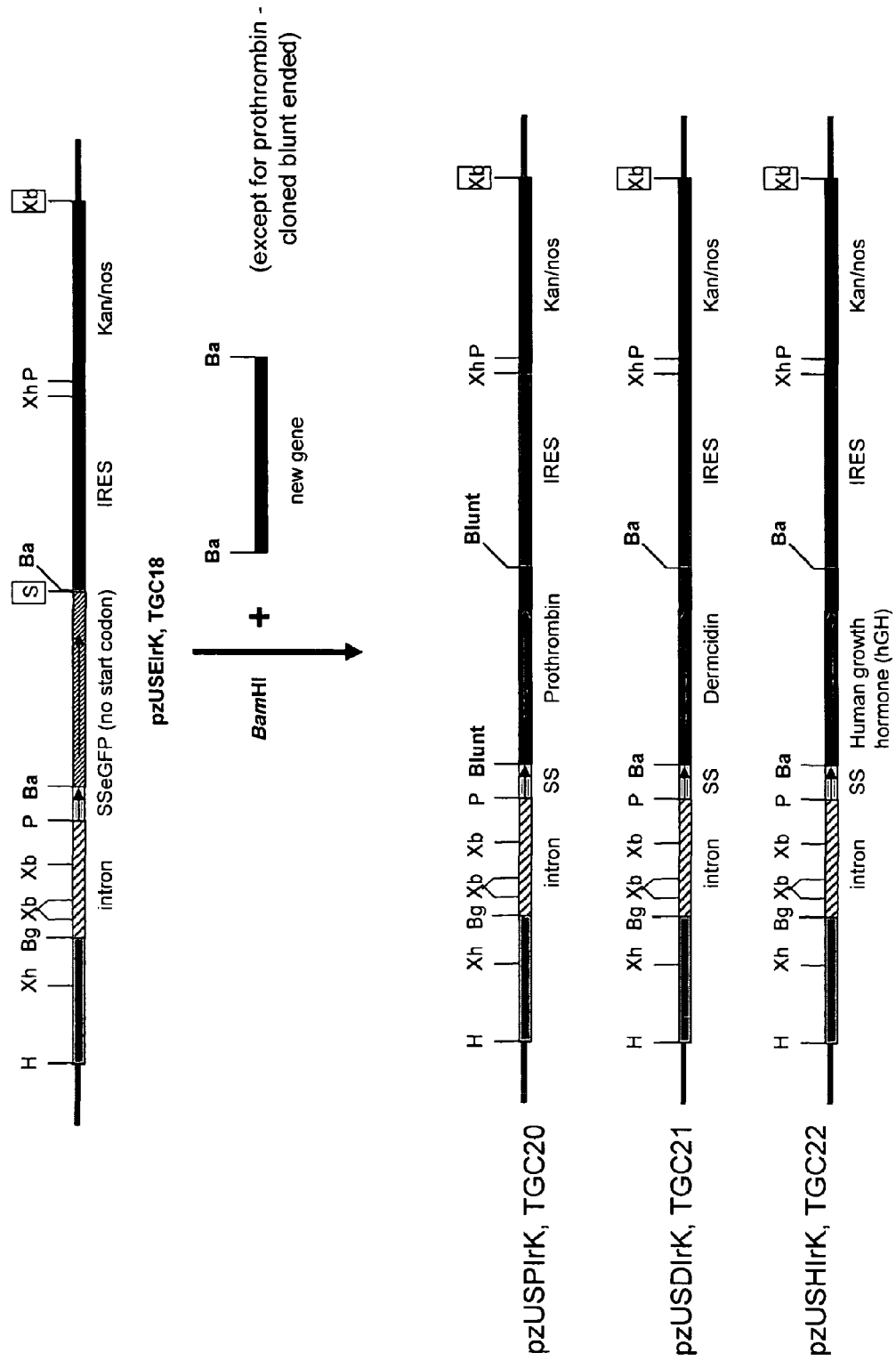

Figure 9
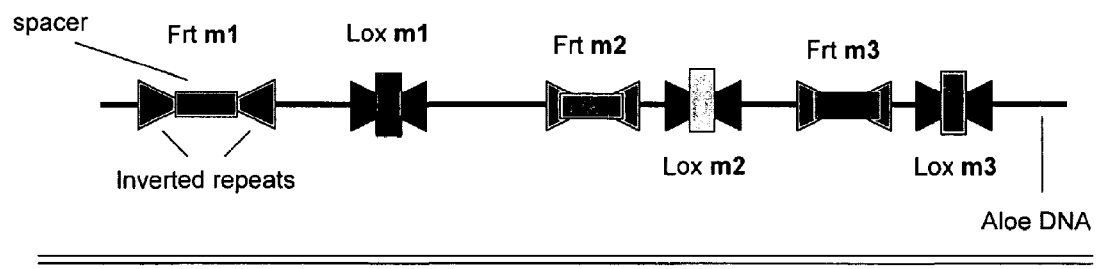
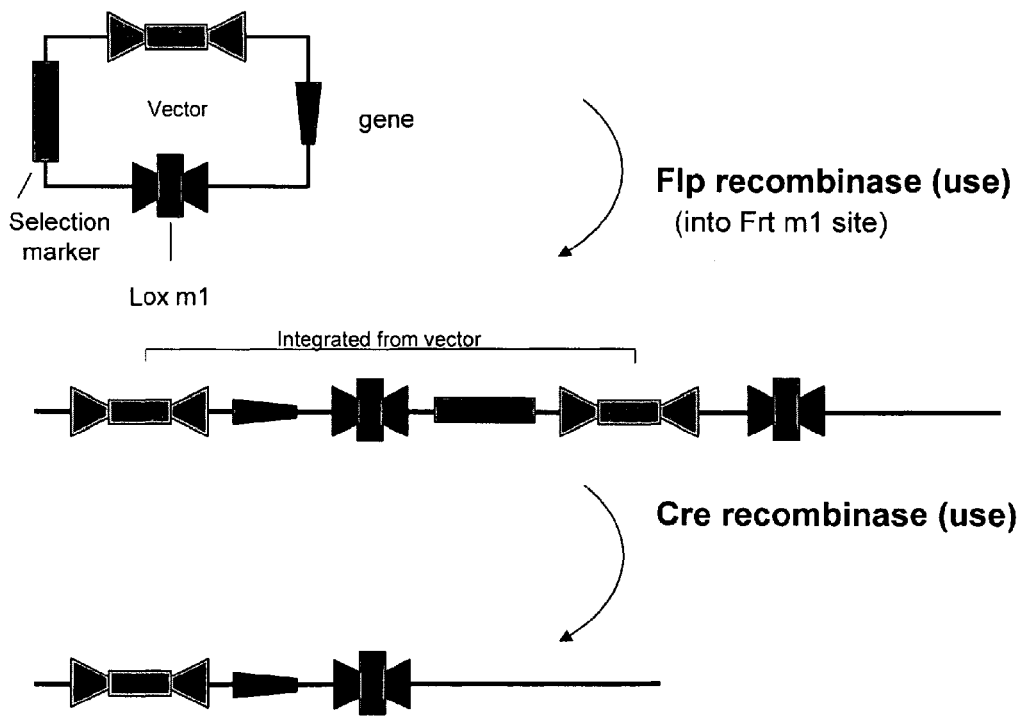

SEQUENCE LISTING

```
<160> NUMBER OF SEQ ID NOS: 46

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaccatggc gcacgtccga ggc                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctactctcca aactgatcaa tga                                              23

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggggatcca ccatgaggtt catgactctc                                       30
```

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcggatccc tatagtactg agtcaagg                                      28

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gggggatcca ccatggctac aggctcccgg                                    30

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggcggatccc tagaagccac agctgccc                                      28

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gggggatcca ccatgaaata tacaagttat                                    30

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tccggatcct taataaatag atttaga                                       27

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caactgcagg atccaacaat ggccttgacc tttgctttac                         40

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caactcgagc tcattcctta cttctaaact ttcttg                                 36

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ataggatccg tgagcaaggg cgaggagctg ttc                                    33

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tatgagctct tacttgtaca gctcgtccat gcc                                    33

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cagggatcca ccatggtgag caagggcgag g                                      31

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agtctcgagc ttgtacagct cgtccatgc                                         29

<210> SEQ ID NO 15
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tatctgcaga ccatggtgaa caaacacttc ttgtcccttt cggtcctcat cgtcctcctt       60
ggcctctcct ccaacttgac agccggggga tcc                                    93

```
<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtgaattcgg atcccccggc tgtcaa                                          26

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
attgagctca agcttcgaat tctgcag                                         27

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atactcgagg tggccatatt atcatcgtgt ttttc                                35

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atactcgaga ccatgattga acaagatgga ttgcac                               36

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atttctagac cagagccgcc gccagcattg acagg                                35

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaaccatggc gcacgtccga ggc                                             23
```

```
<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctactctcca aactgatcaa tga                                            23

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gggggatcca ccatgaggtt catgactctc                                     30

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggcggatccc tatagtactg agtcaagg                                       28

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gggggatcca ccatggctac aggctcccgg                                     30

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggcggatccc tagaagccac agctgccc                                       28

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gggggatcca ccatgaaata tacaagttat                                     30
```

```
<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tccggatcct taataaatag atttaga                                              27

<210> SEQ ID NO 29
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctgcagacca tggtgaacaa acacttcttg tccctttcgg tcctcatcgt cctccttggc          60
ctctcctcca acttgacagc cggggatcc                                            90

<210> SEQ ID NO 30
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atgaggttca tgactctcct cttcctgaca gctctggcag gagccctggt ctgtgcctat          60
gatccagagg ccgcctctgc cccaggatcg gggaacccct tgccatgaagc atcagcagct       120 caaaaggaaa atgcaggtga agacccaggg ttagccagac aggcaccaaa gccaaggaag        180
cagagatcca gccttctgga aaaaggccta gacggagcaa aaaaagctgt gggggggactc      240 ggaaaactag gaaaagatgc agtcgaagat ctagaaagcg tgggtaaagg agccgtccat       300
gacgttaaag acgtccttga ctcagtacta tag                                     333

<210> SEQ ID NO 31
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atggtgagca agggcgagga gctgttcacc ggggtggtgc ccatcctggt cgagctggac          60
ggcgacgtaa acggccacaa gttcagcgtg tccggcgagg gcgagggcga tgccacctac        120
ggcaagctga ccctgaagtt catctgcacc accggcaagc tgcccgtgcc ctggcccacc        180
ctcgtgacca cccctgaccta cggcgtgcag tgcttcagcc gctaccccga ccacatgaag      240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
```

```
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 32
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
ggatccacca tggctacagg ctcccggacg tccctgctcc tggcttttgg cctgctctgc     60
ctgccctggc ttcaagaggg cagtgccttc ccaaccattc ccttatccag gcttttttgac   120 aacgctatgc tccgcgccca tcgtctgcac cagctggcct ttgacaccta ccaggagttt   180
gaagaagcct atatcccaaa ggaacagaag tattcattcc tgcagaaccc ccagacctcc   240
ctctgtttct cagagtctat tccgacaccc tccaacaggg aggaaacaca acagaaatcc   300
aacctagagc tgctccgcat ctccctgctg ctcatccagt cgtggctgga gcccgtgcag   360
ttcctcagga gtgtcttcgc caacagcctg gtgtacggcg cctctgacag caacgtctat   420
gacctcctaa aggacctaga ggaaggcatc caaacgctga tggggaggct ggaagatggc   480
agcccccgga ctgggcagat cttcaagcag acctacagca agttcgacac aaaactcacac   540 aacgatgacg cactactcaa gaactacggg ctgctctact gcttcaggaa ggacatggac   600
aaggtcgaga cattcctgcg catcgtgcag tgccgctctg tgagggcag ctgtggcttc   660 tagggatcc                                                             669
```

<210> SEQ ID NO 33
<211> LENGTH: 570
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
acaatggcct tgacctttgc tttactggtg gccctcctgg tgctcagctg caagtcaagc     60
tgctctgtgg gctgtgatct gcctcaaacc cacagcctgg gtagcaggag gaccttgatg   120
ctcctggcac agatgaggag aatctctctt ttctcctgct tgaaggacag acatgacttt   180
ggatttcccc aggaggagtt tggcaaccag ttccaaaagg ctgaaaccat ccctgtcctc   240
catgagatga tccagcagat cttcaatctc ttcagcacaa aggactcatc tgctgcttgg   300
gatgagaccc tcctagacaa attctacact gaactctacc agcagctgaa tgacctggaa   360
gcctgtgtga tacaggggt gggggtgaca gagactcccc tgatgaagga ggactccatt   420
ctggctgtga ggaaatactt ccaaagaatc actctctatc tgaaagagaa gaaatacagc   480
ccttgtgcct gggaggttgt cagagcagaa atcatgagat ctttttcttt gtcaacaaac   540
ttgcaagaaa gtttaagaag taaggaatga                                      570
```

<210> SEQ ID NO 34
<211> LENGTH: 584
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

| | | | | | |
|---|---|---|---|---|---|
| gccctctcc | ctcccccccc | cctaacgtta | ctggccgaag | ccgcttggaa | taaggccggt | 60 |
| gtgcgtttgt | ctatatgtta | ttttccacca | tattgccgtc | ttttggcaat | gtgagggccc | 120 |
| ggaaacctgg | ccctgtcttc | ttgacgagca | ttcctagggg | tctttcccct | ctcgccaaag | 180 |
| gaatgcaagg | tctgttgaat | gtcgtgaagg | aagcagttcc | tctggaagct | tcttgaagac | 240 |
| aaacaacgtc | tgtagcgacc | ctttgcaggc | agcggaaccc | cccacctggc | gacaggtgcc | 300 |
| tctgcggcca | aaagccacgt | gtataagata | cacctgcaaa | ggcggcacaa | ccccagtgcc | 360 |
| acgttgtgag | ttggatagtt | gtggaaagag | tcaaatggct | ctcctcaagc | gtattcaaca | 420 |
| aggggctgaa | ggatgcccag | aaggtacccc | attgtatggg | atctgatctg | ggcctcggt | 480 |
| gcacatgctt | tacatgtgtt | tagtcgaggt | taaaaaaacg | tctaggcccc | ccgaaccacg | 540 |
| gggacgtggt | tttcctttga | aaaacacgat | gataatatgg | ccac | | 584 |

<210> SEQ ID NO 35
<211> LENGTH: 1469
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

| | | | | | |
|---|---|---|---|---|---|
| atgattgaac | aagatggatt | gcacgcaggt | tctccggccg | cttgggtgga | gaggctattc | 60 |
| ggctatgact | gggcacaaca | gacaatcggc | tgctctgatg | ccgccgtgtt | ccggctgtca | 120 |
| gcgcaggggc | gcccggttct | ttttgtcaag | accgacctgt | ccggtgccct | gaatgaactg | 180 |
| caggacgagg | cagcgcggct | atcgtggctg | gccacgacgg | gcgttccttg | cgcagctgtg | 240 |
| ctcgacgttg | tcactgaagc | gggaagggac | tggctgctat | tgggcgaagt | gccggggcag | 300 |
| gatctcctgt | catctcacct | tgctcctgcc | gagaaagtat | ccatcatggc | tgatgcaatg | 360 |
| cggcggctgc | atacgcttga | tccggctacc | tgcccattcg | accaccaagc | gaaacatcgc | 420 |
| atcgagcgag | cacgtactcg | gatggaagcc | ggtcttgtcg | atcaggatga | tctggacgaa | 480 |
| gagcatcagg | ggctcgcgcc | agccgaactg | ttcgccaggc | tcaaggcgcg | catgcccgac | 540 |
| ggcgatgatc | tcgtcgtgac | ccatggcgat | gcctgcttgc | cgaatatcat | ggtggaaaat | 600 |
| ggccgctttt | ctggattcat | cgactgtggc | cggctgggtg | tggcggaccg | ctatcaggac | 660 |
| atagcgttgg | ctacccgtga | tattgctgaa | gagcttggcg | gcgaatgggc | tgaccgcttc | 720 |
| ctcgtgcttt | acggtatcgc | cgctcccgat | tcgcagcgca | tcgccttcta | tcgccttctt | 780 |
| gacgagttct | tctgagcggg | actctggggt | tcgaaatgac | cgaccaagcg | acgcccaacc | 840 |
| tgccatcacg | agatttcgat | tccaccgccg | ccttctatga | aaggttgggc | ttcggaatcg | 900 |
| ttttccggga | cgccggctgg | atgatcctcc | agcgcgggga | tctcatgctg | gagttcttcg | 960 |
| cccacgggat | ctctgcggaa | caggcggtcg | aaggtgccga | tatcattacg | acagcaacgg | 1020 |
| ccgacaagca | caacgccacg | atcctgagcg | acaatatgat | cgggcccggc | gtccacatca | 1080 |
| acggcgtcgg | cggcgactgc | ccaggcaaga | ccgagatgca | ccgcgatatc | ttgctgcgtt | 1140 |
| cggatatttt | cgtggagttc | ccgccacaga | cccggatgat | ccccgatcgt | tcaaacattt | 1200 |
| ggcaataaag | tttcttaaga | ttgaatcctg | ttgccggtct | tgcgatgatt | atcatataat | 1260 |
| ttctgttgaa | ttacgttaag | catgtaataa | ttaacatgta | atgcatgacg | ttatttatga | 1320 |

```
gatgggtttt tatgattaga gtcccgcaat tatacattta atacgcgata gaaaacaaaa    1380
tatagcgcgc aaactaggat aaattatcgc gcgcggtgtc atctatgtta ctagatcggg    1440
cctcctgtca atgctggcgg cggctctgg                                      1469
```

<210> SEQ ID NO 36
<211> LENGTH: 1874
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
aaaccatggc gcacgtccga ggcttgcagc tgcctggctg cctggccctg gctgccctgt      60
gtagccttgt gcacagccag catgtgttcc tggctcctca gcaagcacgg tcgctgctcc     120
agcgggtccg gcgagccaac accttcttgg aggaggtgcg caagggcaac ctagagcgag     180
agtgcgtgga ggagacgtgc agctacgagg aggccttcga ggctctggag tcctccacgg     240
ctacggatgt gttctgggcc aagtacacag cttgtgagac agcgaggacg cctcgagata     300
agcttgctgc atgtctggaa ggtaactgtg ctgagggtct gggtacgaac taccgagggc     360
atgtgaacat cacccggtca ggcattgagt gccagctatg gaggagtcgc tacccacata     420
agcctgaaat caactccact acccatcctg gggccgacct acaggagaat ttctgccgca     480
accccgacag cagcaccacg ggaccctggt gctacactac agaccccacc gtgaggaggc     540
aggaatgcag catccctgtc tgtggccagg atcaagtcac tgtagcgatg actccacgct     600
ccgaaggctc cagtgtgaat ctgtcacctc cattggagca gtgtgtccct gatcgggggc     660
agcagtacca ggggcgcctg gcggtgacca cacatgggct cccctgcctg gcctgggcca     720
gcgcacaggc caaggccctg agcaagcacc aggacttcaa ctcagctgtg cagctggtgg     780
agaacttctg ccgcaaccca gacggggatg aggagggcgt gtggtgctat gtggccggga     840
agcctggcga ctttgggtac tgcgacctca actattgtga ggaggccgtg gaggaggaga     900
caggagatgg gctggatgag gactcagaca gggccatcga agggcgtacc gccaccagtg     960
agtaccagac tttcttcaat ccgaggacct ttggctcggg agaggcagac tgtgggctgc    1020
gacctctgtt cgagaagaag tcgctggagg acaaaaccga agagagctc ctggaatcct     1080 acatcgacgg gcgcattgtg agggctcgg atgcagagat cggcatgtca ccttggcagg    1140
tgatgctttt ccggaagagt ccccaggagc tgctgtgtgg ggccagcctc atcagtgacc    1200
gctgggtcct caccgccgcc cactgcctcc tgtacccgcc ctgggacaag aacttcaccg    1260
agaatgacct tctggtgcgc attggcaagc actcccgcac aaggtacgag cgaaacattg    1320
aaaagatatc catgttggaa aagatctaca tccacccag gtacaactgg cgggagaacc    1380
tggaccggga cattgccctg atgaagctga gaagcctgt tgccttcagt gactacattc    1440
accctgtgtg tctgcccgac agggagacgg cagccagctt gctccaggct ggatacaagg    1500
ggcgggtgac aggctggggc aacctgaagg agacgtggac agccaacgtt ggtaagggc    1560 agcccagtgt cctgcaggtg gtgaacctgc ccattgtgga gcggccggtc tgcaaggact    1620
ccacccggat ccgcatcact gacaacatgt tctgtgctgg ttacaagcct gatgaaggga    1680
aacgagggga tgcctgtgaa ggtgacagtg ggggacccct tgtcatgaag agccccttta    1740 caaccgctg gtatcaaatg ggcatcgtct catggggtga aggctgtgac cgggatggga    1800
aatatggctt ctacacacat gtgttccgcc tgaagaagtg gatacagaag gtcattgatc    1860
```
agtttggaga gtag 1874

<210> SEQ ID NO 37
<211> LENGTH: 4688
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
aagctttgat cccctaatga gcattgcatg tctaagttat aaaaaattac cacatatttt      60
tttgtcacac ttgtttgaag tgcagtttat ctatctttat acatatattt aaacttcact     120
ctacgaataa tataatctat agtactacaa taatatcagt gttttagaga atcatataaa     180
tgaacagtta gacatggtct aaaggacaat tgagtacttt gacaacagga ctctacagtt     240
ttatctcttt agtgtgcatg tgttctcctt ttttttttgca aatagcttca cctatataat     300
acttcatcca ttttattagt acatccattt agggtttagg gttaatggtt tttatagact     360
aattttttta gtacatctat tttattctat tttagcctct aaattaagaa aactaaaact     420
ctattttagt tttttttattt aataatttag atataaaata gaataaaata aagtgactaa     480
aaattaaaca aatacccttt aagaaattaa aaaaactaag gaaacatttt tcttgtttcg     540
agtagataat gccagcctgt taaacgccgt cgacgagtct aacggacacc aaccagcgaa     600
ccagcagcgt cgcgtcgggc caagcgaagc agacggcacg gcatctctgt cgctgcctct     660
gggcccctct cgagagttcc gctccaccgt tggacttgct ccgctgtcgg catccagaaa     720
ttgcgtggcg gagcggcaga cgtgagccgg cacggcaggc ggcctcctcc tcctctcacg     780
gcaccggcag ctacggggga ttccttttccc accgctcctt cgctttccct tcctcgcccg     840
ccgtaataaa tagacacccc ctccacaccc tctttcccca acctcgtgtt gttcggagcg     900
cacacacaca caaccagatc tcccccaaat ccacccgtcg gcacctccgc ttcaaggtac     960
gccgctcgtc ctccccccccc ccctctctac cttctctaga tcggcgttcc ggtccatggt    1020
tagggcccgg tagttctact tctgttcatg tttgtgttag atccgtgttt gtgatagatc    1080
cgtgctgcta gcgttcgtac acggatgcga cctgtacgtc agacacgttc tgattgctaa    1140
cttgccagtg tttctctttg gggaatcctg ggatggctct agccgttccg cagacgggat    1200
cgatttcatg attttttttt gtttcgttgc atagggtttg gtttgccctt tccttttatt    1260
tcaatatatg ccgtgcactt gtttgtcggg tcatctttc atgtttttttt tttggcttgg    1320
ttgtgatgat gtggtctggt tgggcggtcg ttctagatcg gagtagaatt ctgtttcaaa    1380
ctacctggtg gatttattaa ttttggatct gtatgtgtgt gccatacata ttcatagtta    1440
cgaattgaag atgatggatg gaaatatcga tctaggatag gtatacatgt tgatgcgggt    1500
tttactgatg catatacaga gatgcttttt gttcgcttgg ttgtgatgat gtggtgtggt    1560
tgggcggtcg ttcattcgtt ctagatcgga gtagaatact gtttcaaact aactggtgga    1620
tttattaatt ttggatctgt atgtgtgtgc catacatctt catagttacg agtttaagat    1680
gatggatgga agtatcgatc taggataggt atacatgttg atgtgggttt tactgatgca    1740
tatacatgat ggcatatgca gcatctattc atatgctcta accttgagta cctatctatt    1800
ataataaaca agtatgtttt taattattt tgatcttgat atacttggat gatggcatat    1860
gcagcagcta tatgtggatt ttttttagccc tgccttcata cgctatttat ttgcttggta    1920
ctgtttcttt tgtcgatgct caccctgttg tttggtgtta cttctgcaga ccatggtgaa    1980
```

```
caaacacttc ttgtcccttt cggtcctcat cgtcctcctt ggcctctcct ccaacttgac    2040
agccggggga tccaccatga aatatacaag ttatatcttg gcttttcagc tctgcatcgt    2100
tttgggttct cttggctgtt actgccagga cccatatgta aaagaagcag aaaaccttaa    2160
gaaatatttt aatgcaggtc attcagatgt agcggataat ggaactcttt tcttaggcat    2220
tttgaagaat tggaaagagg agagtgacag aaaaataatg cagagccaaa ttgtctcctt    2280
ttacttcaaa cttttaaaa actttaaaga tgaccagagc atccaaaaga gtgtggagac    2340
catcaaggaa gacatgaatg tcaagttttt caatagcaac aaaaagaaac gagatgactt    2400
cgaaaagctg actaattatt cggtaactga cttgaatgtc aacgcaaag caatacatga     2460 actcatccaa gtgatggctg aactgtcgcc agcagctaaa acagggaagc gaaaaggag     2520 tcagatgctg tttcgaggtc gaagagcatc ccagtaatgg ttgtcctgcc tgcaatattt    2580
gaattttaaa tctaaatcta tttattaagg atccggatcc gccctctcc ctcccccccc     2640 cctaacgtta ctggccgaag ccgcttggaa taaggccggt gtgcgtttgt ctatatgtta    2700
ttttccacca tattgccgtc ttttggcaat gtgagggccc ggaaacctgg ccctgtcttc    2760
ttgacgagca ttcctagggg tctttcccct ctcgccaaag gaatgcaagg tctgttgaat    2820
gtcgtgaagg aagcagttcc tctggaagct tcttgaagac aaacaacgtc tgtagcgacc    2880
ctttgcaggc agcggaaccc cccacctggc gacaggtgcc tctgcggcca aaagccacgt    2940
gtataagata cacctgcaaa ggcggcacaa ccccagtgcc acgttgtgag ttggatagtt    3000
gtggaaagag tcaaatggct ctcctcaagc gtattcaaca aggggctgaa ggatgcccag    3060
aaggtacccc attgtatggg atctgatctg gggcctcggt gcacatgctt acatgtgtt     3120 tagtcgaggt taaaaaaacg tctaggcccc ccgaaccacg gggacgtggt tttcctttga    3180
aaaacacgat gataatatgg ccacctcgag accatgattg aacaagatgg attgcacgca    3240
ggttctccgg ccgcttgggt ggagaggcta ttcggctatg actgggcaca acagacaatc    3300
ggctgctctg atgccgccgt gttccggctg tcagcgcagg ggcgcccggt tcttttgtc     3360 aagaccgacc tgtccggtgc cctgaatgaa ctgcaggacg aggcagcgcg gctatcgtgg    3420
ctggccacga cgggcgttcc ttgcgcagct gtgctcgacg ttgtcactga agcgggaagg    3480
gactggctgc tattgggcga agtgccgggg caggatctcc tgtcatctca ccttgctcct    3540
gccgagaaag tatccatcat ggctgatgca atgcggcggc tgcatacgct tgatccggct    3600
acctgcccat tcgaccacca agcgaaacat cgcatcgagc gagcacgtac tcggatggaa    3660
gccggtcttg tcgatcagga tgatctggac gaagagcatc aggggctcgc gccagccgaa    3720
ctgttcgcca ggctcaaggc gcgcatgccc gacggcgatg atctcgtcgt gacccatggc    3780
gatgcctgct tgccgaatat catggtggaa aatggccgct tttctggatt catcgactgt    3840
ggccggctgg gtgtggcgga ccgctatcag gacatagcgt tggctacccg tgatattgct    3900
gaagagcttg gcggcgaatg ggctgaccgc ttcctcgtgc tttacggtat cgccgctccc    3960
gattcgcagc gcatcgcctt ctatcgcctt cttgacgagt tcttctgagc gggactctgg    4020
ggttcgaaat gaccgaccaa gcgacgccca acctgccatc acgagatttc gattccaccg    4080
ccgccttcta tgaaaggttg gcttcggaa tcgttttccg gacgccggc tggatgatcc      4140 tccagcgcgg ggatctcatg ctggagttct tcgcccacgg atctctgcg gaacaggcgg    4200 tcgaaggtgc cgatatcatt acgacagcaa cggccgacaa gcacaacgcc acgatcctga    4260
gcgacaatat gatcgggccc ggcgtccaca tcaacgcgcg cggcggcgac tgcccaggca    4320
agaccgagat gcaccgcgat atcttgctgc gttcggatat tttcgtggag ttcccgccac    4380
```

-continued

```
agacccggat gatccccgat cgttcaaaca tttggcaata aagtttctta agattgaatc    4440
ctgttgccgg tcttgcgatg attatcatat aatttctgtt gaattacgtt aagcatgtaa    4500
taattaacat gtaatgcatg acgttattta tgagatgggt ttttatgatt agagtcccgc    4560
aattatacat ttaatacgcg atagaaaaca aaatatagcg cgcaaactag gataaattat    4620
cgcgcgcggt gtcatctatg ttactagatc gggcctcctg tcaatgctgg cggcggctct    4680
ggtctaga                                                            4688
```

<210> SEQ ID NO 38
<211> LENGTH: 4178
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
aagctttgat ccctaatga gcattgcatg tctaagttat aaaaaattac cacatatttt      60
tttgtcacac ttgtttgaag tgcagtttat ctatctttat acatatattt aaacttcact    120
ctacgaataa tataatctat agtactacaa taatatcagt gttttagaga atcatataaa    180
tgaacagtta gacatggtct aaaggacaat tgagtacttt gacaacagga ctctacagtt    240
ttatctcttt agtgtgcatg tgttctcctt ttttttttgca aatagcttca cctatataat    300
acttcatcca ttttattagt acatccattt agggtttagg gttaatggtt tttatagact    360
aattttttta gtacatctat tttattctat tttagcctct aaattaagaa aactaaaact    420
ctattttagt ttttttattt aataatttag atataaaata gaataaaata aagtgactaa    480
aaattaaaca aatacccttt aagaaattaa aaaaactaag gaaacatttt tcttgtttcg    540
agtagataat gccagcctgt taaacgccgt cgacgagtct aacggacacc aaccagcgaa    600
ccagcagcgt cgcgtcgggc caagcgaagc agacggcacg gcatctctgt cgctgcctct    660 gggccctct cgagagttcc gctccaccgt tggacttgct ccgctgtcgg catccagaaa    720
ttgcgtggcg gagcggcaga cgtgagccgg acggcaggc ggcctcctcc tcctctcacg    780
gcaccggcag ctacggggga ttccttccc accgctcctt cgctttccct cctcgcccg    840 ccgtaataaa tagacacccc ctccacaccc tctttcccca acctcgtgtt gttcggagcg    900
cacacacaca caaccagatc tcccccaaat ccacccgtcg gcacctccgc ttcaaggtac    960
gccgctcgtc ctcccccccc ccctctctac cttctctaga tcggcgttcc ggtccatggt   1020
tagggcccgg tagttctact tctgttcatg tttgtgttag atccgtgttt gtgatagatc   1080
cgtgctgcta gcgttcgtac acggatgcga cctgtacgtc agacacgttc tgattgctaa   1140
cttgccagtg tttctctttg gggaatcctg ggatggctct agccgttccg cagacgggat   1200
cgatttcatg attttttttt gtttcgttgc atagggtttg gtttgccctt ttcctttatt   1260
tcaatatatg ccgtgcactt gtttgtcggg tcatcttttc atgtttttt tttggcttgg   1320 ttgtgatgat gtggtctggt tgggcggtcg ttctagatcg gagtagaatt ctgtttcaaa   1380
ctacctggtg gatttattaa ttttggatct gtatgtgtgt gccatacata ttcatagtta   1440
cgaattgaag atgatggatg gaaatatcga tctaggatag gtatacatgt tgatgcgggt   1500
tttactgatg catatacaga gatgcttttt gttcgcttgg ttgtgatgat gtggtgtggt   1560
tgggcggtcg ttcattcgtt ctagatcgga gtagaatact gtttcaaact aactggtgga   1620
tttattaatt ttggatctgt atgtgtgtgc catacatctt catagttacg agtttaagat   1680
```

```
gatggatgga agtatcgatc taggataggt atacatgttg atgtgggttt tactgatgca   1740
tatacatgat ggcatatgca gcatctattc atatgctcta accttgagta cctatctatt   1800
ataataaaca agtatgtttt ataattattt tgatcttgat atacttggat gatggcatat   1860
gcagcagcta tatgtggatt tttttagccc tgccttcata cgctatttat ttgcttggta   1920
ctgtttcttt tgtcgatgct caccctgttg tttggtgtta cttctgcagg atccaccatg   1980
gtgagcaagg gcgaggagct gttcaccggg gtggtgccca tcctggtcga gctggacggc   2040
gacgtaaacg gccacaagtt cagcgtgtcc ggcgagggcg agggcgatgc cacctacggc   2100
aagctgaccc tgaagttcat ctgcaccacc ggcaagctgc ccgtgccctg gcccaccctc   2160
gtgaccaccc tgacctacgg cgtgcagtgc ttcagccgct accccgacca catgaagcag   2220
cacgacttct tcaagtccgc catgcccgaa ggctacgtcc aggagcgcac catcttcttc   2280
aaggacgacg gcaactacaa gacccgcgcc gaggtgaagt tcgagggcga caccctggtg   2340
aaccgcatcg agctgaaggg catcgacttc aaggaggacg gcaacatcct ggggcacaag   2400
ctggagtaca actacaacag ccacaacgtc tatatcatgg ccgacaagca agaacggc    2460 atcaaggtga acttcaagat ccgccacaac atcgaggacg gcagcgtgca gctcgccgac   2520
cactaccagc agaacacccc catcggcgac ggccccgtgc tgctgcccga caaccactac   2580
ctgagcaccc agtccgccct gagcaaagac cccaacgaga gcgcgatca catggtcctg   2640 ctggagttcg tgaccgccgc cgggatcact ctcggcatgg acgagctgta caagctcgag   2700
accatgattg aacaagatgg attgcacgca ggttctccgg ccgcttgggt ggagaggcta   2760
ttcggctatg actgggcaca acagacaatc ggctgctctg atgccgccgt gttccggctg   2820
tcagcgcagg ggcgcccggt tcttttgtc aagaccgacc tgtccggtgc cctgaatgaa   2880
ctgcaggacg aggcagcgcg gctatcgtgg ctggccacga cgggcgttcc ttgcgcagct   2940
gtgctcgacg ttgtcactga agcgggaagg gactggctgc tattgggcga agtgccgggg   3000
caggatctcc tgtcatctca ccttgctcct gccgagaaag tatccatcat ggctgatgca   3060
atgcggcggc tgcatacgct tgatccggct acctgcccat tcgaccacca agcgaaacat   3120
cgcatcgagc gagcacgtac tcggatggaa gccggtcttg tcgatcagga tgatctggac   3180
gaagagcatc aggggctcgc gccagccgaa ctgttcgcca ggctcaaggc gcgcatgccc   3240
gacggcgatg atctcgtcgt gacccatggc gatgcctgct tgccgaatat catggtggaa   3300
aatggccgct ttctggatt catcgactgt ggccggctgg gtgtggcgga ccgctatcag   3360
gacatagcgt tggctacccg tgatattgct gaagagcttg gcggcgaatg ggctgaccgc   3420
ttcctcgtgc tttacggtat cgccgctccc gattcgcagc gcatcgcctt ctatcgcctt   3480
cttgacgagt tcttctgagc gggactctgg ggttcgaaat gaccgaccaa gcgacgccca   3540
acctgccatc acgagattc gattccaccg ccgccttcta tgaaaggttg gcttcggaa    3600 tcgttttccg gacgccggc tggatgatcc tccagcgcgg ggatctcatg ctggagttct   3660
tcgcccacgg gatctctgcg gaacaggcgg tcgaaggtgc cgatatcatt acgacagcaa   3720
cggccgacaa gcacaacgcc acgatcctga gcgacaatat gatcgggccc ggcgtccaca   3780
tcaacggcgt cggcggcgac tgcccaggca agaccgagat gcaccgcgat atcttgctgc   3840
gttcggatat tttcgtggag ttccgccac agacccggat gatccccgat cgttcaaaca   3900
tttggcaata aagtttctta agattgaatc ctgttgccgg tcttgcgatg attatcatat   3960
aatttctgtt gaattacgtt aagcatgtaa taattaacat gtaatgcatg acgttattta   4020
```

```
tgagatgggt ttttatgatt agagtcccgc aattatacat ttaatacgcg atagaaaaca    4080
aaatatagcg cgcaaactag gataaattat cgcgcgcggt gtcatctatg ttactagatc    4140
gggcctcctg tcaatgctgg cggcggctct ggtctaga                            4178
```

<210> SEQ ID NO 39
<211> LENGTH: 4663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
aagctttgat cccctaatga gcattgcatg tctaagttat aaaaaattac cacatatttt      60
tttgtcacac ttgtttgaag tgcagtttat ctatctttat acatatattt aaacttcact     120
ctacgaataa tataatctat agtactacaa taatatcagt gttttagaga atcatataaa     180
tgaacagtta gacatggtct aaaggacaat tgagtacttt gacaacagga ctctacagtt     240
ttatctcttt agtgtgcatg tgttctcctt ttttttttgca aatagcttca cctatataat    300
acttcatcca ttttattagt acatccattt agggtttagg gttaatggtt tttatagact     360
aattttttta gtacatctat tttattctat tttagcctct aaattaagaa aactaaaact     420
ctattttagt ttttttattt aataatttag atataaaata gaataaaata aagtgactaa     480
aaattaaaca aatacccttt aagaaattaa aaaaactaag gaaacatttt tcttgtttcg     540
agtagataat gccagcctgt taaacgccgt cgacgagtct aacggacacc aaccagcgaa     600
ccagcagcgt cgcgtcgggc caagcgaagc agacggcacg gcatctctgt cgctgcctct     660
gggcccctct cgagagttcc gctccaccgt tggacttgct ccgctgtcgg catccagaaa     720
ttgcgtggcg gagcggcaga cgtgagcggg cacggcaggc ggcctcctcc tcctctcacg     780
gcaccggcag ctacggggga ttccttcccc accgctcctt cgctttccct tcctcgcccg     840
ccgtaataaa tagacacccc ctccacaccc tctttcccca acctcgtgtt gttcggagcg     900
cacacacaca caaccagatc tccccccaaat ccacccgtcg gcacctccgc ttcaaggtac     960
gccgctcgtc ctccccccccc ccctctctac cttctctaga tcggcgttcc ggtccatggt    1020
tagggcccgg tagttctact tctgttcatg tttgtgttag atccgtgttt gtgatagatc    1080
cgtgctgcta gcgttcgtac acggatgcga cctgtacgtc agacacgttc tgattgctaa    1140
cttgccagtg tttctctttg gggaatcctg ggatggctct agccgttccg cagacgggat    1200
cgatttcatg atttttttttt gtttcgttgc atagggtttg gtttgccctt ttcctttatt    1260
tcaatatatg ccgtgcactt gtttgtcggg tcatcttttc atgtttttttt tttggcttgg    1320 ttgtgatgat gtggtctggt tgggcggtcg ttctagatcg gagtagaatt ctgtttcaaa    1380
ctacctggtg gatttattaa ttttggatct gtatgtgtgt gccatacata ttcatagtta    1440
cgaattgaag atgatggatg gaaatatcga tctaggatag gtatacatgt tgatgcgggt    1500
tttactgatg catatacaga gatgcttttt gttcgcttgg ttgtgatgat gtggtgtggt    1560
tgggcggtcg ttcattcgtt ctagatcgga gtagaatact gtttcaaact aactggtgga    1620
tttattaatt ttggatctgt atgtgtgtgc catacatctt catagttacg agtttaagat    1680
gatggatgga agtatcgatc taggataggt atacatgttg atgtgggttt tactgatgca    1740
tatacatgat ggcatatgca gcatctattc atatgctcta accttgagta cctatctatt    1800
ataataaaca agtatgtttt ataattattt tgatcttgat atacttggat gatggcatat    1860
```

-continued

```
gcagcagcta tatgtggatt tttttagccc tgccttcata cgctatttat ttgcttggta    1920
ctgtttcttt tgtcgatgct caccctgttg tttggtgtta cttctgcagg atccaacaat    1980
ggccttgacc tttgctttac tggtggccct cctggtgctc agctgcaagt caagctgctc    2040
tgtgggctgt gatctgcctc aaacccacag cctgggtagc aggaggacct tgatgctcct    2100
ggcacagatg aggagaatct ctcttttctc ctgcttgaag acagacatg actttggatt     2160
tccccaggag gagtttggca accagttcca aaaggctgaa accatccctg tcctccatga    2220
gatgatccag cagatcttca atctcttcag cacaaaggac tcatctgctg cttgggatga    2280
gaccctccta gacaaattct acactgaact ctaccagcag ctgaatgacc tggaagcctg    2340
tgtgatacag ggggtggggg tgacagagac tcccctgatg aaggaggact ccattctggc    2400
tgtgaggaaa tacttccaaa gaatcactct ctatctgaaa gagaagaaat acagcccttg    2460
tgcctgggag gttgtcagag cagaaatcat gagatctttt tctttgtcaa caaacttgca    2520
agaaagttta agaagtaagg aatgagagct caagcttcga attctgcagt cgacggtacc    2580
gcgggcccgg gatccgcccc tctccctccc ccccccctaa cgttactggc cgaagccgct    2640
tggaataagg ccggtgtgcg tttgtctata tgttattttc caccatattg ccgtcttttg    2700
gcaatgtgag ggcccggaaa cctggccctg tcttcttgac gagcattcct aggggtcttt    2760
cccctctcgc caaggaatg caaggtctgt tgaatgtcgt gaaggaagca gttcctctgg     2820
aagcttcttg aagacaaaca acgtctgtag cgacccttg caggcagcgg aaccccccac     2880
ctggcgacag gtgcctctgc ggccaaaagc cacgtgtata agatacacct gcaaaggcgg    2940
cacaacccca gtgccacgtt gtgagttgga tagttgtgga aagagtcaaa tggctctcct    3000
caagcgtatt caacaagggg ctgaaggatg cccagaaggt accccattgt atgggatctg    3060
atctggggcc tcggtgcaca tgctttacat gtgtttagtc gaggttaaaa aaacgtctag    3120
gccccccgaa ccacggggac gtggttttcc tttgaaaaac acgatgataa tatggccacc    3180
tcgagaccat gattgaacaa gatggattgc acgcaggttc tccggccgct tgggtggaga    3240
ggctattcgg ctatgactgg gcacaacaga caatcggctg ctctgatgcc gccgtgttcc    3300
ggctgtcagc gcaggggcgc ccggttcttt ttgtcaagac cgacctgtcc ggtgccctga    3360
atgaactgca ggacgaggca gcgcggctat cgtggctggc cacgacgggc gttccttgcg    3420
cagctgtgct cgacgttgtc actgaagcgg gaagggactg gctgctattg ggcgaagtgc    3480
cggggcagga tctcctgtca tctcaccttg ctcctgccga gaaagtatcc atcatggctg    3540
atgcaatgcg gcggctgcat acgcttgatc cggctacctg cccattcgac caccaagcga    3600
aacatcgcat cgagcgagca cgtactcgga tggaagccgg tcttgtcgat caggatgatc    3660
tggacgaaga gcatcagggg ctcgcgccag ccgaactgtt cgccaggctc aaggcgcgca    3720
tgcccgacgg cgatgatctc gtcgtgaccc atggcgatgc ctgcttgccg aatatcatgg    3780
tggaaaatgg ccgcttttct ggattcatcg actgtggccg ctgggtgtg gcggaccgct     3840
atcaggacat agcgttggct acccgtgata ttgctgaaga gcttggcggc gaatgggctg    3900
accgcttcct cgtgctttac ggtatcgccg ctcccgattc gcagcgcatc gccttctatc    3960
gccttcttga cgagttcttc tgagcggac tctgggttc gaaatgaccg accaagcgac      4020
gcccaacctg ccatcacgag atttcgattc caccgccgcc ttctatgaaa ggttgggctt    4080
cggaatcgtt ttccgggacg ccggctggat gatcctccag cgcgggatc tcatgctgga    4140
gttcttcgcc cacgggatct ctgcggaaca ggcggtcgaa ggtgccgata tcattacgac    4200
agcaacggcc gacaagcaca acgccacgat cctgagcgac aatatgatcg gcccggcgt     4260
```

```
ccacatcaac ggcgtcggcg gcgactgccc aggcaagacc gagatgcacc gcgatatctt    4320
gctgcgttcg gatattttcg tggagttccc gccacagacc cggatgatcc ccgatcgttc    4380
aaacatttgg caataaagtt tcttaagatt gaatcctgtt gccggtcttg cgatgattat    4440
catataattt ctgttgaatt acgttaagca tgtaataatt aacatgtaat gcatgacgtt    4500
atttatgaga tgggttttta tgattagagt cccgcaatta tacatttaat acgcgataga    4560
aaacaaaata tagcgcgcaa actaggataa attatcgcgc gcggtgtcat ctatgttact    4620
agatcgggcc tcctgtcaat gctggcggcg gctctggtct aga                     4663
```

<210> SEQ ID NO 40
<211> LENGTH: 4463
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
aagctttgat cccctaatga gcattgcatg tctaagttat aaaaaattac cacatatttt      60
tttgtcacac ttgtttgaag tgcagtttat ctatctttta acatatatttt aaacttcact    120 ctacgaataa tataatctat agtactacaa taatatcagt gttttagaga atcatataaa    180
tgaacagtta gacatggtct aaaggacaat tgagtacttt gacaacagga ctctacagtt    240
ttatctcttt agtgtgcatg tgttctcctt tttttttgca aatagcttca cctatataat    300
acttcatcca ttttattagt acatccattt agggtttagg gttaatggtt tttatagact    360 aatttttttta gtacatctat tttattctat tttagcctct aaattaagaa aactaaaact    420
ctattttagt tttttttattt aataatttag atataaaata gaataaaata aagtgactaa    480
aaattaaaca aatacccttt aagaaattaa aaaaactaag gaaacatttt tcttgtttcg    540
agtagataat gccagcctgt taaacgccgt cgacgagtct aacggacacc aaccagcgaa    600
ccagcagcgt cgcgtcgggc caagcgaagc agacggcacg gcatctctgt cgctgcctct    660 gggccctct cgagagttcc gctccaccgt tggacttgct ccgctgtcgg catccagaaa    720
ttgcgtggcg gagcggcaga cgtgagccgg cacggcaggc ggcctcctcc tcctctcacg    780
gcaccggcag ctacggggga ttcctttccc accgctcctt cgctttcctt cctcgcccg    840 ccgtaataaa tagacacccc ctccacaccc tctttcccca acctcgtgtt gttcggagcg    900
cacacacaca caaccagatc tcccccaaat ccaccccgtcg gcacctccgc ttcaaggtac    960
gccgctcgtc ctccccccc ccctctctac cttctctaga tcggcgttcc ggtccatggt   1020
tagggcccgg tagttctact tctgttcatg tttgtgttag atccgtgttt gtgatagatc   1080
cgtgctgcta gcgttcgtac acggatgcga cctgtacgtc agacacgttc tgattgctaa   1140
cttgccagtg tttctctttg gggaatcctg ggatggctct agccgttccg cagacgggat   1200
cgatttcatg atttttttttt gtttcgttgc atagggtttg gtttgccctt tcctttatt    1260 tcaatatatg ccgtgcactt gtttgtcggg tcatctttttc atgttttttt tttggcttgg   1320
ttgtgatgat gtggtctggt tgggcggtcg ttctagatcg gagtagaatt ctgtttcaaa   1380
ctacctggtg gatttattaa ttttggatct gtatgtgtgt gccatacata ttcatagtta    1440
cgaattgaag atgatggatg gaaatatcga tctaggatag gtacatgt tgatgcgggt     1500 tttactgatg catatacaga gatgcttttt gttcgcttgg ttgtgatgat gtggtgtggt   1560
tgggcggtcg ttcattcgtt ctagatcgga gtagaatact gtttcaaact aactggtgga   1620
```

```
tttattaatt ttggatctgt atgtgtgtgc catacatctt catagttacg agtttaagat    1680
gatggatgga agtatcgatc taggataggt atacatgttg atgtgggttt tactgatgca    1740
tatacatgat ggcatatgca gcatctattc atatgctcta accttgagta cctatctatt    1800
ataataaaca agtatgtttt ataattattt tgatcttgat atacttggat gatggcatat    1860
gcagcagcta tatgtggatt tttttagccc tgccttcata cgctatttat ttgcttggta    1920
ctgtttcttt tgtcgatgct caccctgttg tttggtgtta cttctgcaga ccatggtgaa    1980
caaacacttc ttgtcccttt cggtcctcat cgtcctcctt ggcctctcct ccaacttgac    2040
agccggggga tccaccatga ggttcatgac tctcctcttc ctgacagctc tggcaggagc    2100
cctggtctgt gcctatgatc agaggccgc ctctgcccca ggatcgggga acccttgcca    2160
tgaagcatca gcagctcaaa aggaaaatgc aggtgaagac ccagggttag ccagacaggc    2220
accaaagcca aggaagcaga gatccagcct tctggaaaaa ggcctagacg agcaaaaaa    2280 agctgtgggg ggactcggaa aactaggaaa agatgcagtc gaagatctag aaagcgtggg    2340
taaaggagcc gtccatgacg ttaaagacgt ccttgactca gtactatagg gatccgcccc    2400
tctccctccc ccccccctaa cgttactggc cgaagccgct tggaataagg ccggtgtgcg    2460
tttgtctata tgttatttc caccatattg ccgtcttttg gcaatgtgag ggcccggaaa    2520
cctggccctg tcttcttgac gagcattcct agggtctttt ccctctcgc caaaggaatg    2580 caaggtctgt tgaatgtcgt gaaggaagca gttcctctgg aagcttcttg aagacaaaca    2640
acgtctgtag cgacccttg caggcagcgg aacccccac ctggcgacag gtgcctctgc    2700
ggccaaaagc cacgtgtata agatacacct gcaaaggcgg cacaacccca gtgccacgtt    2760
gtgagttgga tagttgtgga aagagtcaaa tggctctcct caagcgtatt caacaagggg    2820
ctgaaggatg cccagaaggt acccccattgt atgggatctg atctggggcc tcggtgcaca    2880
tgctttacat gtgtttagtc gaggttaaaa aaacgtctag gccccccgaa ccacggggac    2940
gtggttttcc tttgaaaaac acgatgataa tatggccacc tcgagaccat gattgaacaa    3000
gatggattgc acgcaggttc tccggccgct tgggtggaga ggctattcgg ctatgactgg    3060
gcacaacaga caatcggctg ctctgatgcc gccgtgttcc ggctgtcagc gcaggggcgc    3120
ccggttcttt ttgtcaagac cgacctgtcc ggtgccctga tgaactgca ggacgaggca    3180 gcgcggctat cgtggctggc cacgacgggc gttccttgcg cagctgtgct cgacgttgtc    3240
actgaagcgg gaagggactg gctgctattg ggcgaagtgc cggggcagga tctcctgtca    3300
tctcaccttg ctcctgccga gaaagtatcc atcatggctg atgcaatgcg gcggctgcat    3360
acgcttgatc cggctacctg cccattcgac caccaagcga acatcgcat cgagcgagca    3420 cgtactcgga tggaagccgg tcttgtcgat caggatgatc tggacgaaga gcatcagggg    3480
ctcgcgccag ccgaactgtt cgccaggctc aaggcgcgca tgcccgacgg cgatgatctc    3540
gtcgtgaccc atggcgatgc ctgcttgccg aatatcatgg tggaaaatgg ccgcttttct    3600
ggattcatcg actgtggccg ctgggtgtg gcggaccgct atcaggacat agcgttggct    3660
acccgtgata ttgctgaaga gcttggcggc gaatgggctg accgcttcct cgtgctttac    3720
ggtatcgccg ctcccgattc gcagcgcatc gccttctatc gccttcttga cgagttcttc    3780
tgagcgggac tctggggttc gaaatgaccg accaagcgac gcccaacctg ccatcacgag    3840
atttcgattc caccgccgcc ttctatgaaa ggttgggctt cggaatcgtt ttccgggacg    3900
ccggctggat gatcctccag cgcggggatc tcatgctgga gttcttcgcc cacgggatct    3960
```

```
ctgcggaaca ggcggtcgaa ggtgccgata tcattacgac agcaacggcc gacaagcaca    4020
acgccacgat cctgagcgac aatatgatcg gcccggcgt ccacatcaac ggcgtcggcg     4080
gcgactgccc aggcaagacc gagatgcacc gcgatatctt gctgcgttcg gatattttcg    4140
tggagttccc gccacagacc cggatgatcc ccgatcgttc aaacatttgg caataaagtt    4200
tcttaagatt gaatcctgtt gccggtcttg cgatgattat catataattt ctgttgaatt    4260
acgttaagca tgtaataatt aacatgtaat gcatgacgtt atttatgaga tgggttttta    4320
tgattagagt cccgcaatta tacatttaat acgcgataga aaacaaaata tagcgcgcaa    4380
actaggataa attatcgcgc gcggtgtcat ctatgttact agatcgggcc tcctgtcaat    4440
gctggcggcg gctctggtct aga                                            4463
```

<210> SEQ ID NO 41
<211> LENGTH: 4784
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
aagctttgat cccctaatga gcattgcatg tctaagttat aaaaaattac cacatatttt      60
tttgtcacac ttgtttgaag tgcagtttat ctatctttat acatatattt aaacttcact     120
ctacgaataa tataatctat agtactacaa taatatcagt gttttagaga atcatataaa     180
tgaacagtta gacatggtct aaaggacaat tgagtacttt gacaacagga ctctacagtt     240
ttatctcttt agtgtgcatg tgttctcctt ttttttttgca aatagcttca cctatataat    300
acttcatcca ttttattagt acatccattt agggtttagg gttaatggtt tttatagact    360 aatttttta gtacatctat tttattctat tttagcctct aaattaagaa aactaaaact     420
ctattttagt ttttttattt aataatttag atataaaata gaataaaata aagtgactaa    480
aaattaaaca aatacccttt aagaaattaa aaaaactaag gaaacatttt tcttgtttcg    540
agtagataat gccagcctgt taaacgccgt cgacgagtct aacggacacc aaccagcgaa    600
ccagcagcgt cgcgtcgggc caagcgaagc agacggcacg gcatctctgt cgctgcctct    660
gggcccctct cgagagttcc gctccaccgt tggacttgct ccgctgtcgg catccagaaa    720
ttgcgtggcg gagcggcaga cgtgagccgg cacggcaggc ggcctcctcc tcctctcacg    780
gcaccggcag ctacggggga ttccttttccc accgctcctt cgctttccct tcctcgcccg    840
ccgtaataaa tagacacccc ctccacaccc tctttcccca acctcgtgtt gttcggagcg    900
cacacacaca caaccagatc tcccccaaat ccaccgtcg gcacctccgc ttcaaggtac     960
gccgctcgtc ctccccccc cctctctac cttctctaga tcggcgttcc ggtccatggt    1020
tagggcccgg tagttctact tctgttcatg tttgtgttag atccgtgttt gtgatagatc    1080
cgtgctgcta gcgttcgtac acggatgcga cctgtacgtc agacacgttc tgattgctaa    1140
cttgccagtg tttctctttg gggaatcctg ggatggctct agccgttccg cagacgggat    1200
cgatttcatg atttttttt gtttcgttgc atagggtttg gtttgcccct ttcctttatt    1260
tcaatatatg ccgtgcactt gtttgtcggg tcatctttttc atgttttttt tttggcttgg   1320
ttgtgatgat gtggtctggt tgggcggtcg ttctagatcg gagtagaatt ctgtttcaaa    1380
ctacctggtg gatttattaa ttttggatct gtatgtgtgt gccatacata ttcatagtta    1440
cgaattgaag atgatggatg gaaatatcga tctaggatag gtatacatgt tgatgcgggt    1500
```

```
tttactgatg catatacaga gatgcttttt gttcgcttgg ttgtgatgat gtggtgtggt    1560
tgggcggtcg ttcattcgtt ctagatcgga gtagaatact gtttcaaact aactggtgga    1620
tttattaatt ttggatctgt atgtgtgtgc catacatctt catagttacg agtttaagat    1680
gatggatgga agtatcgatc taggataggt atacatgttg atgtgggttt tactgatgca    1740
tatacatgat ggcatatgca gcatctattc atatgctcta accttgagta cctatctatt    1800
ataataaaca agtatgtttt ataattattt tgatcttgat atacttggat gatggcatat    1860
gcagcagcta tatgtggatt ttttagccc tgccttcata cgctatttat ttgcttggta    1920
ctgtttcttt tgtcgatgct caccctgttg tttggtgtta cttctgcaga ccatggtgaa    1980
caaacacttc ttgtcccttt cggtcctcat cgtcctcctt ggcctctcct ccaacttgac    2040
agccggggga tccaccatgg ctacaggctc ccggacgtcc ctgctcctgg cttttggcct    2100
gctctgcctg ccctggcttc aagagggcag tgccttccca accattccct tatccaggct    2160
ttttgacaac gctatgctcc gcgcccatcg tctgcaccag ctggcctttg acacctacca    2220
ggagtttgaa gaagcctata tcccaaagga acagaagtat tcattcctgc agaaccccca    2280
gacctccctc tgtttctcag agtctattcc gacaccctcc aacagggagg aaacacaaca    2340
gaaatccaac ctagagctgc tccgcatctc cctgctgctc atccagtcgt ggctggagcc    2400
cgtgcagttc ctcaggagtg tcttcgccaa cagcctggtg tacggcgcct ctgacagcaa    2460
cgtctatgac ctcctaaagg acctagagga aggcatccaa acgctgatgg gaggctgga    2520 agatggcagc ccccggactg gcagatcttc aagcagacc tacagcaagt cgacacaaa    2580 ctcacacaac gatgacgcac tactcaagaa ctacgggctg ctctactgct tcaggaagga    2640
catggacaag gtcgagacat tcctgcgcat cgtgcagtgc cgctctgtgg agggcagctg    2700
tggcttctag ggatccgccc ctctccctcc cccccccta acgttactgg ccgaagccgc    2760
ttggaataag gccggtgtgc gtttgtctat atgttatttt ccaccatatt gccgtctttt    2820
ggcaatgtga gggcccggaa acctggccct gtcttcttga cgagcattcc tagggggtctt    2880 tcccctctcg ccaaaggaat gcaaggtctg ttgaatgtcg tgaaggaagc agttcctctg    2940
gaagcttctt gaagacaaac aacgtctgta gcgacccttt gcaggcagcg aaccccca    3000 cctggcgaca ggtgcctctg cggccaaaag ccacgtgtat aagatacacc tgcaaaggcg    3060
gcacaacccc agtgccacgt tgtgagttgg atagttgtgg aaagagtcaa atggctctcc    3120
tcaagcgtat tcaacaaggg gctgaaggat gcccagaagg taccccattg tatgggatct    3180
gatctggggc ctcggtgcac atgctttaca tgtgtttagt cgaggttaaa aaaacgtcta    3240 ggcccccga accacgggga cgtggttttc ctttgaaaaa cacgatgata atatggccac    3300
ctcgagacca tgattgaaca agatggattg cacgcaggtt ctccggccgc ttgggtggag    3360
aggctattcg gctatgactg ggcacaacag acaatcggct gctctgatgc cgccgtgttc    3420
cggctgtcag cgcaggggcg cccggttctt tttgtcaaga ccgacctgtc cggtgccctg    3480
aatgaactgc aggacgaggc agcgcggcta tcgtggctgg ccacgacggg cgttccttgc    3540
gcagctgtgc tcgacgttgt cactgaagcg ggaagggact ggctgctatt gggcgaagtg    3600
ccggggcagg atctcctgtc atctcacctt gctcctgccg agaaagtatc catcatggct    3660
gatgcaatgc ggcggctgca tacgcttgat ccggctacct gcccattcga ccaccaagcg    3720
aaacatcgca tcgagcgagc acgtactcgg atggaagccg gtcttgtcga tcaggatgat    3780
ctggacgaag agcatcaggg gctcgcgcca gccgaactgt tcgccaggct caaggcgcgc    3840
atgcccgacg gcgatgatct cgtcgtgacc catggcgatg cctgcttgcc gaatatcatg    3900
```

```
gtggaaaatg gccgcttttc tggattcatc gactgtggcc ggctgggtgt ggcggaccgc   3960
tatcaggaca tagcgttggc tacccgtgat attgctgaag agcttggcgg cgaatgggct   4020
gaccgcttcc tcgtgcttta cggtatcgcc gctcccgatt cgcagcgcat cgccttctat   4080
cgccttcttg acgagttctt ctgagcggga ctctggggtt cgaaatgacc gaccaagcga   4140
cgcccaacct gccatcacga gatttcgatt ccaccgccgc cttctatgaa aggttgggct   4200
tcggaatcgt tttccgggac gccggctgga tgatcctcca gcgcgggat ctcatgctgg   4260 agttcttcgc ccacgggatc tctgcggaac aggcggtcga aggtgccgat atcattacga   4320
cagcaacggc cgacaagcac aacgccacga tcctgagcga caatatgatc gggcccggcg   4380
tccacatcaa cggcgtcggc ggcgactgcc caggcaagac cgagatgcac cgcgatatct   4440
tgctgcgttc ggatattttc gtggagttcc cgccacagac ccggatgatc cccgatcgtt   4500
caaacatttg gcaataaagt ttcttaagat tgaatcctgt tgccggtctt gcgatgatta   4560
tcatataatt tctgttgaat tacgttaagc atgtaataat taacatgtaa tgcatgacgt   4620
tatttatgag atgggttttt atgattagag tcccgcaatt atacatttaa tacgcgatag   4680
aaaacaaaat atagcgcgca aactaggata aattatcgcg cgcggtgtca tctatgttac   4740
tagatcgggc ctcctgtcaa tgctggcggc ggctctggtc taga                   4784

<210> SEQ ID NO 42
<211> LENGTH: 5991
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
aagctttgat cccctaatga gcattgcatg tctaagttat aaaaaattac cacatatttt     60
tttgtcacac ttgtttgaag tgcagtttat ctatctttat acatatattt aaacttcact    120
ctacgaataa tataatctat agtactacaa taatatcagt gttttagaga atcatataaa    180
tgaacagtta gacatggtct aaaggacaat tgagtacttt gacaacagga ctctacagtt    240
ttatctcttt agtgtgcatg tgttctcctt ttttttgca aatagcttca cctatataat    300
acttcatcca ttttattagt acatccattt aggggttagg gttaatggtt tttatagact    360 aatttttta gtacatctat tttattctat tttagcctct aaattaagaa aactaaaact    420
ctattttagt ttttttattt aataatttag atataaaata gaataaaata aagtgactaa    480
aaattaaaca aatacccttt aagaaattaa aaaaactaag gaaacatttt tcttgtttcg    540
agtagataat gccagcctgt taaacgccgt cgacgagtct aacggacacc aaccagcgaa    600
ccagcagcgt cgcgtcgggc caagcgaagc agacggcacg gcatctctgt cgctgcctct    660
gggcccctct cgagagttcc gctccaccgt tggacttgct ccgctgtcgg catccagaaa    720
ttgcgtggcg gagcggcaga cgtgagccgg cacggcaggc ggcctcctcc tcctctcacg    780
gcaccggcag ctacggggga ttccttccc accgctcctt cgctttccct tcctcgcccg    840
ccgtaataaa tagacacccc ctccacaccc tctttcccca acctcgtgtt gttcggagcg    900
cacacacaca caaccagatc tccccaaat ccaccgtcg gcacctccgc ttcaaggtac    960
gccgctcgtc ctccccccccc ccctctctac cttctctaga tcggcgttcc ggtccatggt   1020
tagggcccga tagttctact tctgttcatg tttgtgttag atccgtgttt gtgatagatc   1080
cgtgctgcta gcgttcgtac acggatgcga cctgtacgtc agacacgttc tgattgctaa   1140
```

```
cttgccagtg tttctctttg gggaatcctg ggatggctct agccgttccg cagacgggat    1200
cgatttcatg atttttttt gtttcgttgc atagggtttg gtttgccctt ttcctttatt    1260
tcaatatatg ccgtgcactt gtttgtcggg tcatcttttc atgttttttt tttggcttgg    1320
ttgtgatgat gtggtctggt tgggcggtcg ttctagatcg gagtagaatt ctgtttcaaa    1380
ctacctggtg gatttattaa ttttggatct gtatgtgtgt gccatacata ttcatagtta    1440
cgaattgaag atgatggatg gaaatatcga tctaggatag gtatacatgt tgatgcgggt    1500
tttactgatg catatacaga gatgctttt gttcgcttgg ttgtgatgat gtggtgtggt    1560
tgggcggtcg ttcattcgtt ctagatcgga gtagaatact gtttcaaact aactggtgga    1620
tttattaatt ttggatctgt atgtgtgtgc catacatctt catagttacg agtttaagat    1680
gatggatgga agtatcgatc taggataggt atacatgttg atgtgggttt tactgatgca    1740
tatacatgat ggcatatgca gcatctattc atatgctcta accttgagta cctatctatt    1800
ataataaaca agtatgtttt ataattattt tgatcttgat atacttggat gatggcatat    1860
gcagcagcta tatgtggatt ttttttagccc tgccttcata cgctatttat ttgcttggta    1920
ctgtttcttt tgtcgatgct caccctgttg tttggtgtta cttctgcaga ccatggtgaa    1980
caaacacttc ttgtcccttt cggtcctcat cgtcctcctt ggcctctcct ccaacttgac    2040
agccggggaa accatggcgc acgtccgagg cttgcagctg cctggctgcc tggcctggc     2100 tgccctgtgt agccttgtgc acagccagca tgtgttcctg gctcctcagc aagcacggtc    2160
gctgctccag cgggtccggc gagccaacac cttcttggag gaggtgcgca agggcaacct    2220
agagcgagag tgcgtggagg agacgtgcag ctacgaggag gccttcgagg ctctggagtc    2280 ctccacgget acggatgtgt ctgggccaa gtacacagct tgtgagacag cgaggacgcc    2340
tcgagataag cttgctgcat gtctggaagg taactgtgct gagggtctgg gtacgaacta    2400
ccgagggcat gtgaacatca cccggtcagg cattgagtgc cagctatgga ggagtcgcta    2460
cccacataag cctgaaatca actccactac ccatcctggg gccgacctac aggagaattt    2520
ctgccgcaac cccgacagca gcaccacggg accctggtgc tacactacag accccaccgt    2580
gaggaggcag gaatgcagca tccctgtctg tggccaggat caagtcactg tagcgatgac    2640
tccacgctcc gaaggctcca gtgtgaatct gtcacctcca ttggagcagt gtgtccctga    2700 tcggggcag cagtaccagg ggcgcctggc ggtgaccaca catgggctcc cctgcctggc    2760
ctgggccagc gcacaggcca aggccctgag caagcaccag gacttcaact cagctgtgca    2820
gctggtggag aacttctgcc gcaacccaga cggggatgag gagggcgtgt ggtgctatgt    2880
ggccgggaag cctggcgact ttgggtactg cgacctcaac tattgtgagg aggccgtgga    2940
ggaggagaca ggagatgggc tggatgagga ctcagacagg gccatcgaag gcgtaccgc     3000 caccagtgag taccagactt tcttcaatcc gaggaccttt ggctcgggag aggcagactg    3060
tgggctgcga cctctgttcg agaagaagtc gctggaggac aaaaccgaaa gagctcct     3120 ggaatcctac atcgacgggc gcattgtgga gggctcggat gcagagatcg gcatgtcacc    3180
ttggcaggtg atgcttttcc ggaagagtcc ccaggagctg ctgtgtgggg ccagcctcat    3240
cagtgaccgc tgggtcctca ccgccgccca ctgcctcctg taccccgccct gggacaagaa    3300 cttcaccgag aatgacttc tggtgcgcat ggcaagcac tcccgcacaa ggtacgagcg     3360
aaacattgaa aagatatcca tgttggaaaa gatctcatc caccccaggt acaactggcg    3420
ggagaacctg gaccgggaca ttgccctgat gaagctgaag aagcctgttg ccttcagtga    3480
```

```
ctacattcac cctgtgtgtc tgcccgacag ggagacggca gccagcttgc tccaggctgg    3540
atacaagggg cgggtgacag gctggggcaa cctgaaggag acgtggacag ccaacgttgg    3600 taagggcag cccagtgtcc tgcaggtggt gaacctgccc attgtggagc ggccggtctg     3660
caaggactcc acccggatcc gcatcactga caacatgttc tgtgctggtt acaagcctga    3720 tgaaggaaa cgagggatg cctgtgaagg tgacagtggg ggacccttg tcatgaagag       3780 cccctttaac aaccgctggt atcaaatggg catcgtctca tggggtgaag gctgtgaccg    3840
ggatgggaaa tatggcttct acacacatgt gttccgcctg aagaagtgga tacagaaggt    3900
cattgatcag tttggagagt agcgcccctc tccctccccc cccctaacg ttactggccg     3960 aagccgcttg gaataaggcc ggtgtgcgtt tgtctatatg ttattttcca ccatattgcc    4020
gtcttttggc aatgtgaggg cccggaaacc tggccctgtc ttcttgacga gcattcctag   4080
gggtctttcc cctctcgcca aggaatgca aggtctgttg aatgtcgtga aggaagcagt    4140
tcctctggaa gcttcttgaa acaaacaac gtctgtagcg accctttgca ggcagcggaa    4200 cccccacct ggcgacaggt gcctctgcgg ccaaaagcca cgtgtataag atacacctgc    4260
aaaggcggca aaccccagt gccacgttgt gagttggata gttgtggaaa gagtcaaatg    4320
gctctcctca agcgtattca acaagggct gaaggatgcc cagaaggtac cccattgtat    4380
gggatctgat ctggggcctc ggtgcacatg ctttacatgt gtttagtcga ggttaaaaaa    4440
acgtctaggc cccccgaacc acgggacgt ggttttcctt tgaaaaacac gatgataata    4500
tggccacctc gagaccatga ttgaacaaga tggattgcac gcaggttctc cggccgcttg    4560
ggtggagagg ctattcggct atgactgggc acaacagaca atcggctgct ctgatgccgc    4620
cgtgttccgg ctgtcagcgc aggggcgccc ggttcttttt gtcaagaccg acctgtccgg    4680
tgccctgaat gaactgcagg acgaggcagc gcggctatcg tggctggcca cgacgggcgt    4740
tccttgcgca gctgtgctcg acgttgtcac tgaagcggga agggactggc tgctattggg    4800
cgaagtgccg gggcaggatc tcctgtcatc tcaccttgct cctgccgaga agtatccat    4860 catggctgat gcaatgcggc ggctgcatac gcttgatccg gctacctgcc cattcgacca    4920
ccaagcgaaa catcgcatcg agcgagcacg tactcggatg gaagccggtc ttgtcgatca    4980
ggatgatctg gacgaagagc atcaggggct cgcgccagcc gaactgttcg ccaggctcaa    5040
ggcgcgcatg cccgacggcg atgatctcgt cgtgacccat ggcgatgcct gcttgccgaa    5100
tatcatggtg gaaaatggcc gcttttctgg attcatcgac tgtggccggc tgggtgtggc    5160
ggaccgctat caggacatag cgttggctac ccgtgatatt gctgaagagc ttggcggcga    5220
atgggctgac cgcttcctcg tgctttacgg tatcgccgct cccgattcgc agcgcatcgc    5280
cttctatcgc cttcttgacg agttcttctg agcgggactc tggggttcga atgaccgac    5340 caagcgacgc ccaacctgcc atcacgagat ttcgattcca ccgccgcctt ctatgaaagg    5400
ttgggcttcg gaatcgtttt ccgggacgcc ggctggatga tcctccagcg cggggatctc    5460
atgctggagt tcttcgccca cgggatctct gcggaacagg cggtcgaagg tgccgatatc    5520
attacgacag caacggccga caagcacaac gccacgatcc tgagcgacaa tatgatcggg    5580
cccggcgtcc acatcaacgg cgtcggcggc gactgcccag gcaagaccga gatgcaccgc    5640
gatatcttgc tgcgttcgga tattttcgtg gagttcccgc cacagacccg atgatccccc    5700
gatcgttcaa acatttggca ataaagtttc ttaagattga atcctgttgc cggtcttgcg    5760
atgattatca tataatttct gttgaattac gttaagcatg taataattaa catgtaatgc    5820
atgacgttat ttatgagatg ggtttttatg attagagtcc cgcaattata catttaatac    5880
```

```
gcgatagaaa acaaaatata gcgcgcaaac taggataaat tatcgcgcgc ggtgtcatct    5940
atgttactag atcgggcctc ctgtcaatgc tggcggcggc tctggtctag a             5991

<210> SEQ ID NO 43
<211> LENGTH: 4888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
aagctttgat cccctaatga gcattgcatg tctaagttat aaaaaattac cacatatttt      60
tttgtcacac ttgtttgaag tgcagtttat ctatctttat acatatattt aaacttcact     120
ctacgaataa tataatctat agtactacaa taatatcagt gttttagaga atcatataaa     180
tgaacagtta gacatggtct aaaggacaat tgagtacttt gacaacagga ctctacagtt     240
ttatctcttt agtgtgcatg tgttctcctt ttttttttgca aatagcttca cctatataat     300
acttcatcca ttttattagt acatccattt agggtttagg gttaatggtt tttatagact     360 aatttttta gtacatctat tttattctat tttagcctct aaattaagaa aactaaaact     420
ctattttagt ttttttattt aataatttag atataaaata gaataaaata aagtgactaa     480
aaattaaaca aataccctt aagaaattaa aaaaactaag gaaacatttt tcttgtttcg     540
agtagataat gccagcctgt taaacgccgt cgacgagtct aacggacacc aaccagcgaa     600
ccagcagcgt cgcgtcgggc caagcgaagc agacggcacg gcatctctgt cgctgcctct     660 gggccctct cgagagttcc gctccaccgt tggacttgct ccgctgtcgg catccagaaa     720 tgcgtggcg gagcggcaga cgtgagccgg cacggcaggc ggcctcctcc tcctctcacg     780
gcaccggcag ctacggggga ttccttcc accgctcctt cgctttccct tcctcgcccg     840
ccgtaataaa tagacacccc ctccacaccc tctttcccca acctcgtgtt gttcggagcg     900
cacacacaca caaccagatc tcccccaaat ccaccgtcg gcacctccgc ttcaaggtac     960
gccgctcgtc ctccccccc ccctctctac cttctctaga tcggcgttcc ggtccatggt    1020 tagggccgg tagttctact tctgttcatg tttgtgttag atccgtgttt gtgatagatc    1080
cgtgctgcta gcgttcgtac acggatgcga cctgtacgtc agacacgttc tgattgctaa    1140
cttgccagtg tttctctttg gggaatcctg ggatggctct agccgttccg cagacgggat    1200
cgatttcatg atttttttt gtttcgttgc ataggggtttg gtttgccctt ttcctttatt    1260
tcaatatatg ccgtgcactt gtttgtcggg tcatctttc atgttttttt tttggcttgg    1320
ttgtgatgat gtggtctggt tgggcggtcg ttctagatcg gagtagaatt ctgtttcaaa    1380
ctacctggtg gatttattaa ttttggatct gtatgtgtgt gccatacata ttcatagtta    1440
cgaattgaag atgatggatg gaaatatcga tctaggatag gtacacatgt tgatgcgggt    1500
tttactgatg catatacaga gatgcttttt gttcgcttgg ttgtgatgat gtggtgtggt    1560
tgggcggtcg ttcattcgtt ctagatcgga gtagaatact gtttcaaact aactggtgga    1620
tttattaatt ttggatctgt atgtgtgtgc catacatctt catagttacg agtttaagat    1680
gatggatgga agtatcgatc taggataggt atacatgttg atgtgggttt tactgatgca    1740
tatacatgat ggcatatgca gcatctattc atatgctcta accttgagta cctatctatt    1800
ataataaaca agtatgtttt ataattattt tgatcttgat atacttggat gatggcatat    1860
gcagcagcta tatgtggatt tttttagccc tgccttcata cgctatttat ttgcttggta    1920
```

```
ctgtttcttt tgtcgatgct caccctgttg tttggtgtta cttctgcaga ccatggtgaa    1980
caaacacttc ttgtcccttt cggtcctcat cgtcctcctt ggcctctcct ccaacttgac    2040
agccggggga tccgtgagca agggcgagga gctgttcacc ggggtggtgc ccatcctggt    2100
cgagctggac ggcgacgtaa acggccacaa gttcagcgtg tccggcgagg gcgagggcga    2160
tgccacctac ggcaagctga ccctgaagtt catctgcacc accggcaagc tgcccgtgcc    2220
ctggcccacc ctcgtgacca ccctgaccta cggcgtgcag tgcttcagcc gctaccccga    2280
ccacatgaag cagcacgact tcttcaagtc cgccatgccc gaaggctacg tccaggagcg    2340
caccatcttc ttcaaggacg acggcaacta caagacccgc gccgaggtga agttcgaggg    2400
cgacaccctg gtgaaccgca tcgagctgaa gggcatcgac ttcaaggagg acggcaacat    2460
cctggggcac aagctggagt acaactacaa cagccacaac gtctatatca tggccgacaa    2520
gcagaagaac ggcatcaagg tgaacttcaa gatccgccac aacatcgagg acggcagcgt    2580
gcagctcgcc gaccactacc agcagaacac ccccatcggc gacggccccg tgctgctgcc    2640
cgacaaccac tacctgagca cccagtccgc cctgagcaaa gaccccaacg agaagcgcga    2700
tcacatggtc ctgctggagt tcgtgaccgc cgccgggatc actctcggca tggacgagct    2760
gtacaagtaa gagctcaagc ttcgaattct gcagtcgacg gtaccgcggg cccgggatcc    2820
gcccctctcc ctcccccccc cctaacgtta ctggccgaag ccgcttggaa taaggccggt    2880
gtgcgtttgt ctatatgtta ttttccacca tattgccgtc ttttggcaat gtgagggccc    2940
ggaaacctgg ccctgtcttc ttgacgagca ttcctagggg tctttcccct ctcgccaaag    3000
gaatgcaagg tctgttgaat gtcgtgaagg aagcagttcc tctggaagct tcttgaagac    3060
aaacaacgtc tgtagcgacc ctttgcaggc agcggaaccc cccacctggc gacaggtgcc    3120
tctgcggcca aaagccacgt gtataagata cacctgcaaa ggcggcacaa ccccagtgcc    3180
acgttgtgag ttggatagtt gtggaaagag tcaaatggct ctcctcaagc gtattcaaca    3240
aggggctgaa ggatgcccag aaggtacccc attgtatggg atctgatctg ggcctcggt     3300 gcacatgctt tacatgtgtt tagtcgaggt taaaaaaacg tctaggcccc ccgaaccacg    3360
gggacgtggt tttcctttga aaaacacgat gataatatgg ccacctcgag accatgattg    3420
aacaagatgg attgcacgca ggttctccgg ccgcttgggt ggagaggcta ttcggctatg    3480
actgggcaca acagacaatc ggctgctctg atgccgccgt gttccggctg tcagcgcagg    3540
ggcgcccggt tcttttttgtc aagaccgacc tgtccggtgc cctgaatgaa ctgcaggacg    3600
aggcagcgcg gctatcgtgg ctggccacga cgggcgttcc ttgcgcagct gtgctcgacg    3660
ttgtcactga agcgggaagg gactggctgc tattgggcga agtgccgggg caggatctcc    3720
tgtcatctca ccttgctcct gccgagaaag tatccatcat ggctgatgca atgcggcggc    3780
tgcatacgct tgatccggct acctgcccat tcgaccacca agcgaaacat cgcatcgagc    3840
gagcacgtac tcggatggaa gccggtcttg tcgatcagga tgatctggac gaagagcatc    3900
aggggctcgc gccagccgaa ctgttcgcca ggctcaaggc gcgcatgccc gacggcgatg    3960
atctcgtcgt gacccatggc gatgcctgct tgccgaatat catggtggaa aatggccgct    4020
tttctggatt catcgactgt ggccggctgg gtgtggcgga ccgctatcag gacatagcgt    4080
tggctacccg tgatattgct gaagagcttg gcggcgaatg ggctgaccgc ttcctcgtgc    4140
tttacggtat cgccgctccc gattcgcagc gcatcgcctt ctatcgcctt cttgacgagt    4200
tcttctgagc gggactctgg ggttcgaaat gaccgaccaa gcgacgccca acctgccatc    4260
```

```
acgagatttc gattccaccg ccgccttcta tgaaaggttg ggcttcggaa tcgttttccg    4320
ggacgccggc tggatgatcc tccagcgcgg ggatctcatg ctggagttct tcgcccacgg    4380
gatctctgcg gaacaggcgg tcgaaggtgc cgatatcatt acgacagcaa cggccgacaa    4440
gcacaacgcc acgatcctga gcgacaatat gatcgggccc ggcgtccaca tcaacggcgt    4500
cggcggcgac tgcccaggca agaccgagat gcaccgcgat atcttgctgc gttcggatat    4560
tttcgtggag ttcccgccac agacccggat gatccccgat cgttcaaaca tttggcaata    4620
aagtttctta agattgaatc ctgttgccgg tcttgcgatg attatcatat aatttctgtt    4680
gaattacgtt aagcatgtaa taattaacat gtaatgcatg acgttattta tgagatgggt    4740
ttttatgatt agagtcccgc aattatacat ttaatacgcg atagaaaaca aaatatagcg    4800
cgcaaactag gataaattat cgcgcgcggt gtcatctatg ttactagatc gggcctcctg    4860
tcaatgctgg cggcggctct ggtctaga                                      4888
```

<210> SEQ ID NO 44
<211> LENGTH: 1963
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
tgatcccta atgagcattg catgtctaag ttataaaaaa ttaccacata ttttttttgtc     60 acacttgttt gaagtgcagt ttatctatct ttatacatat atttaaactt cactctacga    120
ataatataat ctatagtact acaataatat cagtgtttta gagaatcata taaatgaaca    180
gttagacatg gtctaaagga caattgagta cttttgacaac aggactctac agttttatct    240
ctttagtgtg catgtgttct ccttttttttt tgcaaatagc ttcacctata taatacttca    300 tccatttttat tagtacatcc atttaggggtt taggggttaat ggtttttata gactaatttt    360
tttagtacat ctatttttatt ctattttagc ctctaaatta agaaaactaa aactctatttt    420 tagttttttt atttaataat ttagatataa aatagaataa aataaagtga ctaaaaatta    480
aacaaatacc ctttaagaaa ttaaaaaaac taaggaaaca tttttcttgt ttcgagtaga    540
taatgccagc ctgttaaacg ccgtcgacga gtctaacgga caccaaccag cgaaccagca    600
gcgtcgcgtc gggccaagcg aagcagacgg cacggcatct ctgtcgctgc ctctgggccc    660
ctctcgagag ttccgctcca ccgttggact tgctccgctg tcggcatcca gaaattgcgt    720
ggcggagcgg cagacgtgag ccggcacggc aggcggcctc ctcctcctct cacggcaccg    780
gcagctacgg gggattcctt tcccaccgct ccttcgcttt ccttcctcg cccgccgtaa    840 taaatagaca ccccctccac accctctttc cccaaacctcg tgttgttcgg agcgcacaca    900
cacacaacca gatctccccc aaatccaccc gtcggcacct ccgcttcaag gtacgccgct    960
cgtcctcccc cccccctct ctaccttctc tagatcggcg ttccggtcca tggttagggc   1020
ccggtagttc tacttctgtt catgtttgtg ttagatccgt gtttgtgata gatccgtgct   1080
gctagcgttc gtacacggat gcgacctgta cgtcagacac gttctgattg ctaacttgcc   1140
agtgtttctc tttggggaat cctgggatgg ctctagccgt tccgcagacg ggatcgattt   1200 catgatttttt ttttgtttcg ttgcataggg tttggtttgc ccttttcctt tatttcaata   1260
tatgccgtgc acttgtttgt cgggtcatct tttcatgttt tttttttggc ttggttgtga   1320
tgatgtggtc tggttgggcg gtcgttctag atcggagtag aattctgttt caaactacct   1380
```

-continued

```
ggtggattta ttaattttgg atctgtatgt gtgtgccata catattcata gttacgaatt      1440
gaagatgatg gatggaaata tcgatctagg ataggtatac atgttgatgc gggttttact      1500
gatgcatata cagagatgct ttttgttcgc ttggttgtga tgatgtggtg tggttgggcg      1560
gtcgttcatt cgttctagat cggagtagaa tactgtttca aactaactgg tggatttatt      1620
aattttggat ctgtatgtgt gtgccataca tcttcatagt tacgagttta agatgatgga      1680
tggaagtatc gatctaggat aggtatacat gttgatgtgg gttttactga tgcatataca      1740
tgatggcata tgcagcatct attcatatgc tctaaccttg agtacctatc tattataata      1800
aacaagtatg ttttataatt attttgatct tgatatactt ggatgatggc atatgcagca      1860
gctatatgtg gatttttta gccctgcctt catacgctat ttatttgctt ggtactgttt      1920
cttttgtcga tgctcaccct gttgtttggt gttacttctg cag                        1963
```

<210> SEQ ID NO 45
<211> LENGTH: 785
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (123)..(773)

<400> SEQUENCE: 45

```
gcgcaacgca attaatgtga gttagctcac tcattaggca ccccaggctt tacactttat       60
gcttccggct cgtatgttgt gtggaattgt gagcgaataa caatttcaca caggaaacag      120 ct atg acc atg att acg cca agc tat tta ggt gac act ata gaa tac          167
   Met Thr Met Ile Thr Pro Ser Tyr Leu Gly Asp Thr Ile Glu Tyr
   1               5                   10                  15 tca agc tat gca tca agc ttg gta ccg agc tcg gat cca cta gta acg         215
Ser Ser Tyr Ala Ser Ser Leu Val Pro Ser Ser Asp Pro Leu Val Thr
                20                  25                  30 gcc gcc agt gtg ctg gaa ttc tgc aga tat cca tca cac tgg cgg ccg         263
Ala Ala Ser Val Leu Glu Phe Cys Arg Tyr Pro Ser His Trp Arg Pro
            35                  40                  45 ctc gag cat gca tct aga ggg ccc aat tcg ccc tat agt gag tcg tat         311
Leu Glu His Ala Ser Arg Gly Pro Asn Ser Pro Tyr Ser Glu Ser Tyr
        50                  55                  60 tac aat tca ctg gcc gtc gtt tta caa cgt cgt gac tgg gaa aac cct         359
Tyr Asn Ser Leu Ala Val Val Leu Gln Arg Arg Asp Trp Glu Asn Pro
    65                  70                  75 ggc gtt acc caa ctt aat cgc ctt gca gca cat ccc cct ttc gcc agc         407
Gly Val Thr Gln Leu Asn Arg Leu Ala Ala His Pro Pro Phe Ala Ser
80                  85                  90                  95 tgg cgt aat agc gaa gag gcc cgc acc gat cgc cct tcc caa cag ttg         455
Trp Arg Asn Ser Glu Glu Ala Arg Thr Asp Arg Pro Ser Gln Gln Leu
                100                 105                 110 cgc agc cta tac gta cgg cag ttt aag gtt tac acc tat aaa aga gag         503
Arg Ser Leu Tyr Val Arg Gln Phe Lys Val Tyr Thr Tyr Lys Arg Glu
            115                 120                 125 agc cgt tat cgt ctg ttt gtg gat gta cag agt gat att att gac acg         551
Ser Arg Tyr Arg Leu Phe Val Asp Val Gln Ser Asp Ile Ile Asp Thr
        130                 135                 140 ccg ggg cga cgg atg gtg atc ccc ctg gcc agt gca cgt ctg ctg tca         599
Pro Gly Arg Arg Met Val Ile Pro Leu Ala Ser Ala Arg Leu Leu Ser
    145                 150                 155 gat aaa gtc tcc cgt gaa ctt tac ccg gtg gtg cat atc ggg gat gaa         647
Asp Lys Val Ser Arg Glu Leu Tyr Pro Val Val His Ile Gly Asp Glu
```

```
Asp Lys Val Ser Arg Glu Leu Tyr Pro Val Val His Ile Gly Asp Glu
160                 165                 170                 175 agc tgg cgc atg atg acc acc gat atg gcc agt gtg ccg gtc tcc gtt      695
Ser Trp Arg Met Met Thr Thr Asp Met Ala Ser Val Pro Val Ser Val
                180                 185                 190 atc ggg gaa gaa gtg gct gat ctc agc cac cgc gaa aat gac atc aaa      743
Ile Gly Glu Glu Val Ala Asp Leu Ser His Arg Glu Asn Asp Ile Lys
            195                 200                 205 aac gcc att aac ctg atg ttc tgg gga ata taaatgtcag gc                785
Asn Ala Ile Asn Leu Met Phe Trp Gly Ile
            210                 215

<210> SEQ ID NO 46
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Thr Met Ile Thr Pro Ser Tyr Leu Gly Asp Thr Ile Glu Tyr Ser
1               5                   10                  15

Ser Tyr Ala Ser Ser Leu Val Pro Ser Ser Asp Pro Leu Val Thr Ala
            20                  25                  30

Ala Ser Val Leu Glu Phe Cys Arg Tyr Pro Ser His Trp Arg Pro Leu
        35                  40                  45

Glu His Ala Ser Arg Gly Pro Asn Ser Pro Tyr Ser Glu Ser Tyr Tyr
    50                  55                  60

Asn Ser Leu Ala Val Val Leu Gln Arg Arg Asp Trp Glu Asn Pro Gly
65                  70                  75                  80

Val Thr Gln Leu Asn Arg Leu Ala Ala His Pro Pro Phe Ala Ser Trp
                85                  90                  95

Arg Asn Ser Glu Glu Ala Arg Thr Asp Arg Pro Ser Gln Gln Leu Arg
            100                 105                 110

Ser Leu Tyr Val Arg Gln Phe Lys Val Tyr Thr Tyr Lys Arg Glu Ser
        115                 120                 125

Arg Tyr Arg Leu Phe Val Asp Val Gln Ser Asp Ile Ile Asp Thr Pro
    130                 135                 140

Gly Arg Arg Met Val Ile Pro Leu Ala Ser Ala Arg Leu Leu Ser Asp
145                 150                 155                 160

Lys Val Ser Arg Glu Leu Tyr Pro Val Val His Ile Gly Asp Glu Ser
                165                 170                 175

Trp Arg Met Met Thr Thr Asp Met Ala Ser Val Pro Val Ser Val Ile
            180                 185                 190

Gly Glu Glu Val Ala Asp Leu Ser His Arg Glu Asn Asp Ile Lys Asn
        195                 200                 205

Ala Ile Asn Leu Met Phe Trp Gly Ile
    210                 215
```

TRANSGENIC ALOE PLANTS FOR PRODUCTION OF PROTEINS AND RELATED METHODS

CROSS REFERENCE TO RELATED APPLICATIONS

This application is a divisional of U.S. patent application Ser. No. 13/188,815 filed Jul. 22, 2011, now U.S. Pat. No. 8,816,154, which is a divisional of U.S. patent application Ser. No. 11/528,056 filed Sep. 26, 2006, now U.S. Pat. No. 8,008,546, which claims the priority and benefits of U.S. Provisional Application No. 60/720,540 filed Sep. 26, 2005, and which applications are incorporated herein by reference. A claim of priority to all, to the extent appropriate, is made.

INCORPORATION OF SEQUENCE LISTING

The instant application contains a Sequence Listing that has been submitted in ASCII format via EFS-Web, and is hereby incorporated by reference in its entirety. Said ASCII copy, created on Oct. 30, 2012, is named SequenceListing.txt.

BACKGROUND OF THE INVENTION

1. Summary of the Invention

The present inventions relate to transgenic monocot plants and, more particularly, to transgenic aloe plants and methods and compositions for producing a transgenic aloe plant and methods for extracting proteins from the transgenic aloe plants.

2. Description of the Related Art

There continues to be a growing market for biologically active proteins many of which are used for therapeutic purposes. Currently, there are over 160 protein based medicines available. An additional fifty or so are expected to be approved over the next couple of years. Current demand for therapeutic protein production is already outstripping the industry's capacity. It has been predicted that the industry will need to increase its capacity by four to five times to overcome this bottleneck. However, production facilities for therapeutic proteins are expensive and typically take a long time to build. Accordingly, a need exists for production methods that are less expensive and may reduce the time required to ramp up production.

Some animal based protein production methods are used. However, these frequently introduce health risks from diseases. Such risks may arise from cross-contamination with diseases that may affect both the animal and the end user such as a human patient. Accordingly, a need exists for a production method that will eliminate the possibility of cross-contamination between the production organism and the end user.

In addition, many current production methods require extensive processing in order to extract the therapeutic protein from the animal or other host organism in which it was produced and to get the compound into a condition where it may be utilized by a patient. After purification, the protein may be combined with an adjuvant or other carrier material to stabilize the protein and to permit the utilization by a patient. However, the processes of extraction, purification, resuspension among others involved with the processing of a therapeutic protein is complex and cumbersome and may not be conducive to use in underdeveloped countries in need of therapeutics generally. Accordingly, a need exists for simplified production methods which may eliminate or reduce the post extraction processing of therapeutic proteins.

SUMMARY OF THE INVENTION

Compositions and methods in accordance with the present inventions may resolve many of the needs and shortcomings discussed above and will provide additional improvements and advantages as will be recognized by those skilled in the art upon review of the present disclosure.

In one aspect, the present inventions may provide a transgenic aloe plant stably incorporating a gene of interest. In other aspects, novel vectors and constructs may be provided to integrate DNA sequences of interest into the genome of an aloe plant. The sequence of interest may encode for a biologically active protein. The biologically active protein may be interferons, immunoglobulins, lymphokines, growth factors, hormones, blood factors, histocompatability antigens, enzymes, cosmetic proteins and other mammalian proteins, or other proteins of interest. In some aspects, the proteins of interest are human proteins. Aloe plants in accordance with the present inventions may transcribe and translate the gene of interest into the protein of interest. In one aspect, at least some of the protein of interest migrates to a central portion of the aloe leaf. In other aspects, the protein of interest may include a signal sequence to facilitate its translocation into the central portion of the aloe leaf. In other aspects, novel methodologies for the isolation of individual cells from an aloe plant may be provided. In still other aspects, the present inventions may provide novel methods for the integration of vectors into an aloe plant and reproduction of such transgenic aloe plants.

Transgenic aloe plants producing mammalian proteins in accordance with the present inventions may provide a more economically viable alternative for the production of proteins of interest such as for example various biologically active and cosmetic proteins. In one aspect, the proteins of interest may be localized and/or concentrated within the gel of the aloe leaf. This localization of the proteins of interest may simplify the removal of the protein from the plant. In this aspect, the protein of interest may be co-extracted along with the extraction of the native gel within the central portion of the aloe leaf. Accordingly, the present inventions may provide a transgenic plant from which the proteins of interest are generally more readily accessible than those from most transgenic plants such as for example tobacco and corn. Further, the present inventions may provide an efficient method for protein isolation. In still other aspects, the proteins of interest may not be particularly localized within the aloe plant. However, the anatomy and physiology of the aloe plant may still provide certain additional advantages for the production of the protein of interest as will be recognized by those skilled in the art upon review of the present disclosure.

Aloe plants can offer various advantages over conventional methods for producing proteins of interest in bacteria and yeast. The advantages of aloe plants 10 may include the ability to process proteins in ways that the simple single cell bacteria and yeast are poorly suited and which may be necessary to produce the proteins in the desired form. This processing can include the chemical modification, such as by glycosylation, and folding of some proteins for example. Further, in comparison to other protein production methods based on animal cells, aloe plant production may offer significant cost benefits, scalability advantages and a reduced risk of contamination that may be harmful to humans.

A protein modified gel from the central portion of the aloe leaf of a transgenic aloe plant in accordance with the present inventions may be used directly from the aloe plant. This may avoid the need for relatively complex and expensive extraction of the proteins of interest from native plant materials. In some aspects, the gel extracted from the leaf may be used directly without the need for protein extraction or processing. The gel may be in the form of the pith mechanically extracted from an open end of a broken leaf of a transgenic aloe plant.

The present inventions may provide economically viable alternatives for the production of human and other mammalian proteins which are biologically active and/or have cosmetic applications.

Upon review of the present disclosure, those skilled in the art will recognize additional improvements and advantages of the present inventions.

BRIEF DESCRIPTION OF THE DRAWINGS

FIG. 5 lists the sequence information for the ubiquitin promoter from maize and highlights regions of the ubiquitin promoter (SEQ ID NO: 44);

FIGS. 6A and 6B illustrate the construction of a plasmid vector system in accordance with aspects of the present inventions;

FIG. 8 illustrates the construction of additional plasmids vector system in accordance with aspects of the present inventions; and FIG. 9 illustrates the construction of integration systems in accordance with aspects of the present inventions All Figures are illustrated for ease of explanation of the basic teachings of the present inventions only; the extensions of the Figures with respect to number, position, sequence, relationship and compositions of the various embodiments will be explained or will be within the skill of the art after review of the following description. Further, the various protocols, tools, and compositions to practice to disclosed inventions will be within the skill of the art after review of the following description.

DETAILED DESCRIPTION OF THE INVENTIONS

Figure 1:
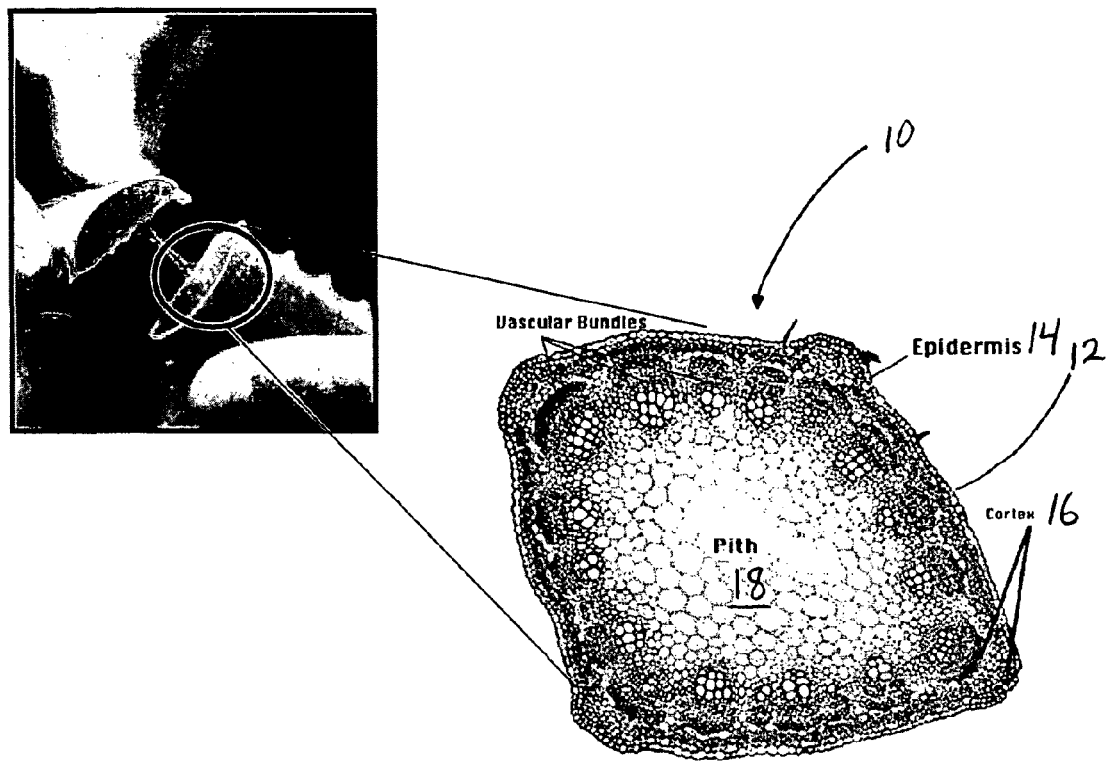
FIG. 1 illustrates an example of the cross-sectional anatomy of an aloe leaf.

As used in the specification, "a" or "an" may mean one or more. As used in the claim(s), when used in conjunction with the word "comprising", the words "a" or "an" may mean one or more than one. As used herein "another" may mean at least a second or more.

As used herein a "transformed aloe cell" means a plant cell that is transformed with stably-integrated, non-natural, recombinant DNA, e.g. by *Agrobacterium*-mediated transformation or by bombardment using microparticles coated with recombinant DNA or other means. A transformed Aloe cell of this inventions can be an originally-transformed plant cell that exists as a microorganism or as a progeny plant cell that is regenerated into differentiated tissue, e.g. into a transgenic Aloe plant 10 with stably-integrated, non-natural recombinant DNA, or seed or pollen derived from a progeny transgenic Aloe plant 10.

As used herein a "transgenic aloe plant" means an aloe plant whose genome has been altered by the stable integration of recombinant DNA. A transgenic aloe plant 10 includes an aloe plant regenerated from an originally-transformed aloe cell and progeny transgenic aloe plants from later generations or crosses of a transformed aloe plant 10.

As used herein "recombinant DNA" means DNA which has been a genetically engineered and constructed outside of a cell including DNA containing naturally occurring DNA, cDNA, synthetic DNA and/or other DNA.

As used herein "promoter" means regulatory DNA for initializing transcription. A "plant promoter" is a promoter capable of initiating transcription in aloe cells whether or not its origin is a aloe cell, e.g. is it well known that *Agrobacterium* promoters are functional in aloe cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions. The promoter may include enhancers or other elements which affect the initiation of transcription, the beginning site of transcription, levels of transcription, the ending site of transcription, or any postprocessing of the resulting ribonucleic acid.

The term "genetic construct" as used herein is defined as a DNA sequence comprising a synthetic arrangement of at least two DNA segments for the purpose of creating a transgenic aloe plant. In a specific embodiment, one segment is a regulatory sequence and another segment encodes a gene product.

As used herein "operably linked" means the association of two or more DNA fragments in a DNA construct so that the function of one, e.g. protein-encoding DNA, is controlled by the other, e.g. a promoter, termination sequence, etc.

The term "transcription" as used herein is defined as the generation of an RNA molecule from a DNA template.

The term "translation" as used herein is defined as the generation of a polypeptide from an RNA template.

As used herein "expressed" means produced, e.g. a protein is expressed in a plant cell when its cognate DNA is transcribed to mRNA that is translated to the protein.

The present inventions may provide novel transgenic aloe plants 10 expressing various proteins of interest, may provide methods and compositions for producing transgenic aloe plants 10, may provide methods for extracting proteins from the transgenic aloe plants 10, and may provides novel compositions of proteins of interest and components from the transgenic aloe plant 10. The proteins of interest produced in accordance with the present inventions may include a secretory signal to facilitate their accumulation in the pith 18 or pith of an aloe leaf 12. In one aspect, this accumulation may occur, at least in part, within the musalegenous cells of the leaf of a transgenic aloe plant 10.

The pith 18 or pulp of an aloe leaf 12 include the components of the leaf which, at least in part, are commonly referred to as the "gel" when extracted from the aloe leaf 12. As used herein, "gel" will refer to the extracted pith 18 and other associated materials which accompany the pith 18 as it is extracted from the aloe leaf 12 regardless of the degree of subsequent processing. In accordance with one or more aspects of the present inventions, the gel from the aloe leaf 12 may have a modified composition. In one particular aspect, the composition of the gel may be modified to include at least one exogenous protein component to be referred to as a "protein modified gel." Extraction of a protein modified gel with the associated protein(s) of interest may offer readily accessible proteins and/or efficient methods for protein isolation. The protein modified gel produced and/or extracted in accordance with the present inventions may be used directly without the need for protein extraction.

Aspects of the present inventions are generally illustrated in FIGS. 1 to 8 for exemplary purposes. The present inventions provide transgenic plants, compositions and methodologies that are generally applicable to the genus *aloe* of the family Liliacae. Typically, the present inventions are described with reference to application in the species is selected from the group of *Aloe vera* (barbadensis miller), *Aloe ferox* and *Aloe arborescence* for exemplary purposes. The Genus *Aloe* generally includes a group of large stemless rosette succulent monocot plants. These plants are generally referred to as aloe plants 10 for purposes of the present disclosure.

Various compounds produced by aloe plants have been used for medicinal purposes. These compounds when present in a protein modified gel may complement the medicinal properties of biologically active proteins of a transgenic aloe plant 10 in accordance with the present inventions. FIG. 1 illustrates a cross section through a leaf 12 of a transgenic aloe plant 10. The leaves of the transgenic aloe plant 10 include an easily extractable gelatinous mixture of proteins, carbohydrates and water included in the gel which is primarily derived from the pith 18. This gelatinous mixture is primarily located in the central portion of an aloe leaf 12. Various compounds in the gel have been shown to have a number of medicinal properties and uses. In one aspect, the gel and/or pith 18 stabilize a transgenic protein produced by a transgenic aloe plant 10 and localized in the gel and/or pith 18.

FIG. 1 particularly illustrates the epidermis 14, the cortex or mesophyll 16, and the pith or pulp 18. The epidermis 14 forms the outer layer of cells of the leaf. In one aspect of the present inventions, a transgenic aloe plant may include aloe cells in one or more of these tissues which transiently or stably incorporate a genetic construct which is expressed by the aloe cell. The cortex 16 includes cells rich in chloroplasts as well as the vascular bundles, xylem and phloem. The pith 18 is the spongy parenchyma composed almost exclusively of large cortex cells and, at least in part, represents the gel where it may be advantageous to incorporate or accumulate one or more transgenic proteins of interest.

The epidermis 14 typically consists of a single outer layer of cells. Just beneath the epidermis 14 is the cortex 16 including the network of vascular bundles. The outer support of the vascular bundles is generally provided by the sheath cells. The vascular bundles are composed of three general types of tubular structures: the xylem, the phloem, and the associated large pericyclic tubules. The xylem transports water and minerals from the roots to the leaf of the plant. The phloem transports starches and other synthesized materials throughout the plant. The pericyclic tubules contain a latex or sap which is very high in the laxative anthraquinones, especially aloin. The anthraquinones absorb ultra violet rays of the sun and prevent overheating of the central portion of the Aloe leaf 12 which generally functions as the water storage organ of the aloe plant. The pericyclic portion of the vascular bundles are adherent to the epidermis 14, while the remainder of the vascular bundles protrude into the pith 18. The innermost and major portion of the aloe leaf 12 is the pith 18 which, at least in part, constitutes the gel. For purposes of gel extraction, the epidermis 14 and cortex 16 may be generally considered to comprise the sheath which contain the gel. The extracted gel, comprised substantially of the pith 18, is typically thick and slimy substance that has been historically been topically applied to skin for medicinal purposes, such as for example as a therapy for burns and wounds.

The gel generally functions as a reservoir of materials for the aloe plant. The cortex 16 typically synthesizes many of the carbohydrates and glycoproteins which are needed by the aloe plant. Carbohydrates synthesized in excess of are typically transported to the pith 18 for storage along with water and some minerals. The carbohydrates are transported by the phloem vessels to large vacuoles within the cortex 16 cells of the pith 18. Water is then osmotically attracted to the carbohydrates permitting the pith 18 to function the water storage organ of the aloe plant.

The gel is relatively easily extracted by breaking an aloe leaf 12 along its longitudinal axis and crushing the leaf to force the gel from the surrounding sheath through the break. Additional materials may extracted from the tissues of the leaf along with the gel.

Process Overview

Transgenic aloe plants 10 in accordance with one or more of the present inventions generally include one or more DNA constructs stably incorporated within the plant to express one or more proteins of interest. Generating a transgenic aloe plant 10 in accordance with one or more of the present inventions may involve a variety of novel compositions and methods. Typically, one or more DNA constructs are developed to express one or more proteins in the transgenic aloe plant 10. In one aspect, a single construct may express a single mRNA. In other aspects, a single construct may express multiple mRNA. In still other aspects, multiple constructs may produce multiple mRNA. Each mRNA may produce one or more polypeptides.

Figure 2:
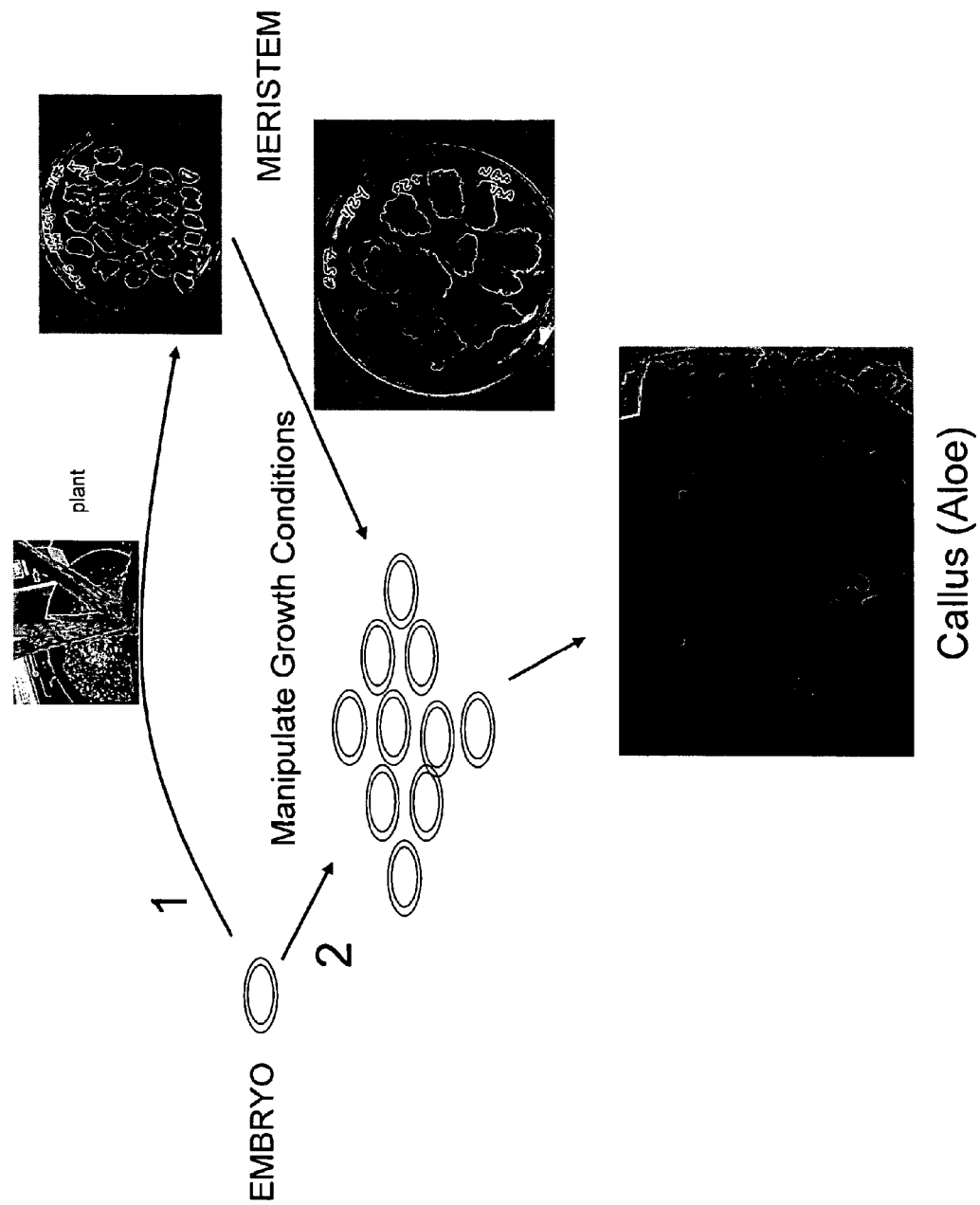
FIG. 2 illustrates exemplary methods for generation of callus tissue.

To introduce the constructs into the aloe plants, aloe cells or undifferentiated callus tissue is typically used as generally illustrated in FIG. 2. The aloe cells and callus tissue are typically derived from the root or leaf meristem tissues or from a seed of an aloe plant. The DNA constructs are introduced into the aloe cells using a range of techniques and/or constructs as is diagrammatically illustrated in FIG. 3. Some techniques will be recognized by those skilled in the art upon review of the present disclosure. Aloe cells or callus tissue incorporating the desired constructs are selected for using various techniques. Typically, the DNA construct will include a selectable marker. Once the desired construct has been stably introduced into the aloe cells or callus tissue, aloe plantlets are typically generated from the aloe cells or callus tissue. The aloe plantlets that develop into viable transgenic aloe plants 10 containing the DNA constructs may either constitutively produce or inducibly produce the desired protein(s) of interest. The protein of interest may be localized in the transgenic aloe plant 10 or may be found generally throughout the transgenic aloe plant 10 depending on the particular protein being produced and/or the presence or absence of a signal sequence associated with the protein.

Depending upon the particular construct and/or associated proteins of interest, the transgenic aloe plant 10 may then be vegetatively or sexually propogated. The proteins may be isolated from the transgenic aloe plants 10 using a wide range of techniques. The proteins may then be further isolated and/or further processed. Such processing may include enzymatic modification, chemical modification, incorporation into a suitable adjuvant, among other processing that will be recognized by those skilled in the art upon review of the present disclosure. In one aspect, the proteins may be processed from an inactive (precursor) into active form for specific applications of the particular protein.

Isolation of Cells

As shown in the exemplary sequence illustrated in FIG. 2, aloe cells or groups of aloe cells are typically isolated from an aloe plant prior to the incorporation of the desired construct. The types of aloe cell generally chosen for incorporation of DNA constructs are generally chosen based on their regenerative potential. Meristematic cells from the shoot meristem or the root meristem from an aloe plant or embryonic aloe cells from an aloe seed may be used. However, many parts of the aloe plant retain the potential to regrow or form callus tissue and may also be utilized. The cells are typically isolated using a range of techniques that will be recognized by those skilled in the art upon review of the present disclosure. Typically, the cells are mechanically isolated from the aloe plant using a scalpel. Alternatively, other techniques mechanical or otherwise may be used to isolate the necessary cells as will be recognized by those skilled in the art upon review of the present disclosure. Once an appropriate aloe cell or group of aloe cells is isolated, the aloe cells are typically grown in culture to form callus tissue. Although certain techniques may not require that the aloe cells are first grown into callus tissue, the callus tissue provides a source of undifferentiated set of aloe cells retaining the potential for generating a transgenic aloe plant 10. The callus tissue is typically grown on a solid medium. However, the callus tissue can also be place in a liquid culture medium and grown in suspension.

The meristematic cells may be isolated from the tips of the roots or leaf of an aloe plant. Meristematic aloe cells may also be isolated from the apical meristem. Typically, the aloe plant from which the tissues are isolated is a young healthy aloe plant. The aloe plant is typically selected to be no larger than eight (8) inches with six (6) or fewer primary shoots. A wound is typically formed on a shoot of an aloe plant by cutting it into segments. The wounded surface may encourage the aloe cells to grow. It is typically primarily on the surface of the cutting that the callus will begin to grow. To isolate aloe cells from an aloe leaf 12, segments are typically cut from the distal end of a young growing shoot. Portions of the segment are then plated on a growth medium. Shoot apical meristem tissue is derived from a one inch cutting from the base of a young aloe plant. The aloe leaves 12 are removed from the cutting and the segment is plated. The meristem aloe cells are found within the "cutting". They are "selected for" or "isolated" by their ability to continue growing on the culture plate—forming callus tissue or regenerating shoots. The meristematic aloe cells once isolated are then cultured on appropriate medium and under conditions promoting the formation of callus tissue.

The isolation of embryonic aloe cells from seeds generally involves removal of the seed coat to expose the embryo and the mechanical removal of the desired aloe cells from the embryo. The aloe seeds are typically sterilized and the outer husks of the seed are removed. To mechanically remove the aloe cells from either a aloe plant or an aloe embryo, a scalpel is typically used. Embryonic aloe cells, once isolated from the seed coat are then cultured on appropriate medium and under conditions promoting the formation of callus tissue.

When callus tissue is desired, the isolated aloe cells are typically grown under conditions favoring the formation of callus tissue as will be recognized by those skilled in the art upon review of the present disclosure. Typically, the isolated aloe cells are plated and grown in an appropriate solid nutrient medium to form callus tissue having a size of roughly 1 cm in diameter prior to transformation. Aloe cells are typically grown between 23 and 26 degrees Celsius. Suitable mediums include a base solid or liquid which will typically include supplemental inorganic nutrients—both macroelements (such as nitrogen, sulphur, phosphorus, calcium, magnesium, and potassium, and microelements (such as iron, boron, cobalt, copper, iodine, manganese, molybdenum, and zinc); organic nutrients including sugars (sucrose or maltose) and vitamins and cofactors (thiamine, niacin, biotin, pyridoxine, myo-inositol among others); amino acids (such as proline and casein hydrolysate); as well as growth regulators primarily a source of auxin (typically (NAA), 1-naphthaleneacetic acid, (IAA), indole-3-acetic acid, or (2,4-D), 2,4-dichlorophenoxyacetic acid) and a source of cytokinin (typically (BAP) 6-benzylaminopurine). These mediums and vitamins are typically commercially available in pre-formulated compositions with varying concentrations of inorganic nutrients and vitamins and are known, among others, as MS media (Murashige-Skoog), Gamborg media, or Chu N6 media. Additionally, cells grown on Petri dishes typically require a solid matrix support such as agar to be added to the growth media.

Formation of DNA Constructs

Suitable DNA constructs are typically introduced into callus tissue derived from isolated aloe cells to allow the production of the protein(s) of interest by the resulting transgenic aloe plant 10. DNA constructs may also be introduced into isolated aloe cells or mature aloe plants as may be recognized by those skilled in the art upon review of the present disclosure. DNA constructs are typically incorporated into a vector such as a plasmid or virus for propagation of the construct and for introduction into the aloe cells. An exemplary plasmid vector may include the plasmid marketed under the tradename pZErO by Invitrogen (Carlsbad, Calif.), diagrammatically illustrated in FIG. 4 for exemplary purposes, and may include one or more of the functional units, for example, of this plasmid.

DNA constructs in accordance with the present inventions can include a promoter sequence capable of functioning in an aloe cell, a sequence encoding a protein of interest, a terminator sequence, and a translational start and stop site all of which are capable of functioning in an aloe cell. These components when properly configured and combined can initiate transcription of DNA and translation of mRNA and their respective termination in an aloe cell. The DNA construct may also include a secretion signal. Alternatively, some proteins of interest, such as for example interferon, may include a domain, natural or synthetic, that targets interferon for secretion. The secretion signal is typically cleaved as the protein leaves the cell or, in some cases, may be retained by the protein without substantially affecting the protein's function. Secretory signals may be added to a variety of proteins that may require secretory signals for translocation. These secretory signals may be derived from various plant secretion sequences. The DNA construct or an associated vector may also include at least one selectable marker. In one aspect, the DNA construct may include both a first selectable marker for propagation of the vector in bacteria and a selectable marker for growth in aloe cells. In addition, the DNA construct may include other regulatory elements as well for expression in specific aloe cells in the aloe plant 10. Other construct components may include additional regulatory elements, such as 5' leaders and introns for enhancing transcription, 3' untranslated regions (such as polyadenylation signals and sites), DNA for transit peptides. Amplification of a desired DNA sequence, such as a sequence encoding a desired therapeutic protein, may be accomplished by the polymerase chain reaction. (see U.S. Pat. Nos. 4,683,202 and 5,928,906, each incorporated herein by reference). Upon review of the present disclosure, those skilled in the art will recognize that the DNA constructs, including the promoter sequences, the regulatory sequences, the stabilizing sequences, the targeting sequences and/or the termination sequences may be modified to affect their function using methods known to those skilled in the art.

As noted above, a promoter that is operable in an aloe cell is typically utilized. The promoter typically contains genetic elements at which regulatory proteins and molecules may bind. These proteins typically include RNA polymerase and other transcription factors. The promoter is operatively linked in a functional location and/or orientation to a nucleic acid sequence to control transcriptional initiation and/or expression of that sequence. The promoter may or may not be used in conjunction with an "enhancer," which refers to a cis-acting regulatory sequence involved in the transcriptional activation of a nucleic acid sequence.

Naturally, it will be important to employ a promoter and/or enhancer that effectively directs the expression of the DNA segment in at least one cell type of an Aloe plant 10 in which expression is desired. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. The DNA constructs typically require transcriptional and translational initiation and termination regulatory signals capable of functioning in aloe cells. A large variety of sequences regulating transcriptional initiation may be used. DNA sequences controlling transcription initiation may come from *Agrobacterium*, viruses or plants. The 35S viral transcription initiation region from cauliflower mosaic virus (35S-CaMV) may be used for aloe plants 10. Plant promoters which may be used in aloe plants 10 may also include the ribulose-1,5-bisphosphate carboxylase (RUBISCO) small subunit promoter from various monocot or dicot plants or the ubiquitin promoter from maize. Other suitable promoters may be used and may be recognized by those skilled in the art upon review of the present disclosure. If inducible regulation is desired, domains may be obtained from different sources so that a regulatory region from one source is combined with an RNA polymerase binding domain from another source. Regulation of expression may be to a particular stage of a transgenic aloe plant's 10 development in a specific part of the transgenic aloe plant 10 like roots, leaves, seeds, flowers, sap or in a combination of plant parts and developmental stages. Regulation of expression to a particular stage of development or tissue may require additional DNA elements as will be recognized by those skilled in the art upon review of the present disclosure.

Numerous other promoters that are active in plant cells have been described in the literature and may be usable in aloe cells. These include promoters present in plant genomes as well as promoters from other sources, including: nopaline synthase (NOS) promoters and octopine synthase (OCS) promoters carried on tumor-inducing plasmids of *Agrobacterium tumefaciens*; and caulimovirus promoters such as the cauliflower mosaic virus. In addition, various other promoters have also been identified in various references, including, but not limited to, U.S. Pat. Nos. 5,858,742 and 5,322,938, which disclose versions of the constitutive promoter derived from cauliflower mosaic virus (CaMV35S); U.S. Pat. No. 5,641,876, which discloses a rice actin promoter; U.S. Patent Application Publication 2002/0192813A1 which discloses 5', 3' and intron elements useful in the design of effective plant expression vectors; U.S. patent application Ser. No. 09/757,089, which discloses a maize chloroplast aldolase promoter; U.S. patent application Ser. No. 08/706,946, which discloses a rice glutelin promoter; U.S. patent application Ser. No. 09/757,089, which discloses a maize aldolase (FDA) promoter; and U.S. patent application Ser. No. 60/310,370, which discloses a maize nicotianamine synthase promoter, all of which are incorporated herein by reference. These and numerous other promoters that function in plant cells and may be operable in a transgenic aloe plant for expression of desired therapeutic proteins.

As one particular example, the ubiquitin promoter (SEQ. ID. NO. 44) from maize may be used. The ubiquitin promoter from maize is a large element, almost 2 kb in length, composed of at least three general regions. The sequence of which is listed in FIG. 5 with the particularly relevant features labeled. The first section of the ubiquitin promoter is located at the most 5' end contains matrix attachment regions (MARs) which are elements that interact with histones and other nuclear proteins and serve to "loop out" flanking sequences making them more readily accessible to the cell's transcriptional machinery. They also help to insulate transcriptional units from one another, which is important in preventing transcription initiated in one place from "reading through" into a second sequence. This may help reduce the risk of creating antisense messages.

The second section contains enhancer elements and the actual promoter. The enhancer elements bind transcription factors that are responsible for directing the transcriptional machinery, the pol II complex, to bind to the promoter and initiate transcription. While the "promoter" specifically refers to the essential DNA elements necessary to interact with the core transcription initiation machinery, the term promoter is more generally used to encompass all of the DNA elements involved with transcription initiation, and in this case the "ubiquitin promoter" is loosely used to mean all of the 2 kb region or modifications of, 5' to the cloned gene of interest.

The third section contains an approximately 1 kb intron. Introns are regions of a transcribed gene that are removed from the final translated message, the mRNA, through the process of splicing. Introns have also been found to influence gene expression directly, by providing alternative enhancer elements, as well as by increasing protein translation by facilitating the translocation of RNA messages from the nucleus to the cytoplasm—a process linked in part to splicing. However, the presence of introns in transgenic systems does not always lead to increases in RNA expression or levels of translated protein. In certain aspects, the ubiquitin intron may be modified to reduce the overall size of the vectors and to assess their effect on transgenic gene expression in the aloe.

In other aspects of the present inventions, it may be desired for preferential expression in green tissues of the aloe plant. Promoters of interest for such uses may include those from genes such as *Arabidopsis thaliana* ribulose-1,5-bisphosphate carboxylase (Rubisco) small subunit (Fischhoff et al. (1992) Plant Mol Biol. 20:81-93), aldolase and pyruvate orthophosphate dikinase (PPDK) (Taniguchi et al. (2000) Plant Cell Physiol. 41(1):42-48).

As noted above, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

Constructs in accordance with aspects of the present inventions may include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene a rice lactate dehydrogenase gene and a rice beta-tubulin gene, all of which are disclosed in U.S. published patent application 2002/0192813 A1, incorporated herein by reference; and the pea (*Pisum sativum*) ribulose biphosphate carboxylase gene (rbs 3'), and 3' elements from the genes within the host plant.

A protein of interest may be encoded by a structural gene incorporated into the DNA construct. The structural gene may be a mammalian gene or portions of a mammalian gene. Structural genes of interest may encode for interferons, immunoglobulins, lymphokines, growth factors, hormones, blood factors, histocompatability antigens, enzymes, or other proteins. The sequence for interferon alpha 2 is listed for exemplary purposes as SEQ. ID. NO. 33. Structural genes may also encode markers proteins like the green fluorescent protein (GFP) from jellyfish. The DNA sequence of the structural genes may be modified to allow high level expression in an aloe plant 10. The codon bias for the aloe plant 10 may differ from the codon bias in the original species from which the structural gene was isolated. The native structural gene may be engineered to optimize the production of the encoded protein in aloe plants 10. Further, the DNA sequence of the structural gene may be engineered to provide for appropriate glycosylation in aloe plants 10 that does not interfere with the structure of the protein.

Termination of transcription and translation may be provided by a variety of transcriptional and translational termination sequences which are capable of functioning in an aloe plant 10. In one aspect, the termination sequences may include the sequence from the nopaline synthetase (NOS) gene from *Agrobacterium*. In other aspect, the termination sequence may be derived from the termination sequences of native aloe genes and proteins.

A marker gene will often be integrated into the DNA construct. The marker gene may allow cells that contain the structural gene of interest to be selected from the population of all cells which do not contain the marker gene. Marker genes may include enzymes or other proteins providing resistance to kanamycin, chloramphenicol, G418 and gentamycin and among others. Still other specific DNA sequences may be necessary if for example *Agrobacterium* is used as a vector. Other regions may be present if the DNA is to be targeted to a specific cell type.

As referenced above, the DNA constructs may also include a secretion signal. Constructs may also include a translocation sequence encoding a signal peptide which may target the therapeutic protein for removal from the cell in which the protein was formed. Various signal sequences have been identified in the literature that are functional in plants and, more particularly, functional in monocot plants such as aloe plants. These may be operably integrated into the constructs or within the genes of interest. In one aspect, the alpha amylase secretory sequence (SEQ. ID NO. 29) from rice (*Oryza sativa*) may be utilized. This signal sequence is characterized in "The alpha-amylase genes in *Oryza sativa*" Mol Gen Genet., 1990 April; 221(2):235-44, the disclosure of which is hereby incorporated by reference in its entirety. Alternatively, some genes of interest, such as for example interferon, may include a domain, natural or synthetic, that targets interferon for secretion. The secretion signal is typically cleaved as the protein leaves the cell or, in some cases, may be retained by the protein without substantially affecting the protein's function. Secretory signals may be added to a variety of proteins that may require secretory signals for translocation. These secretory sequences may be derived from various plant secretion sequences.

Figure 6B:
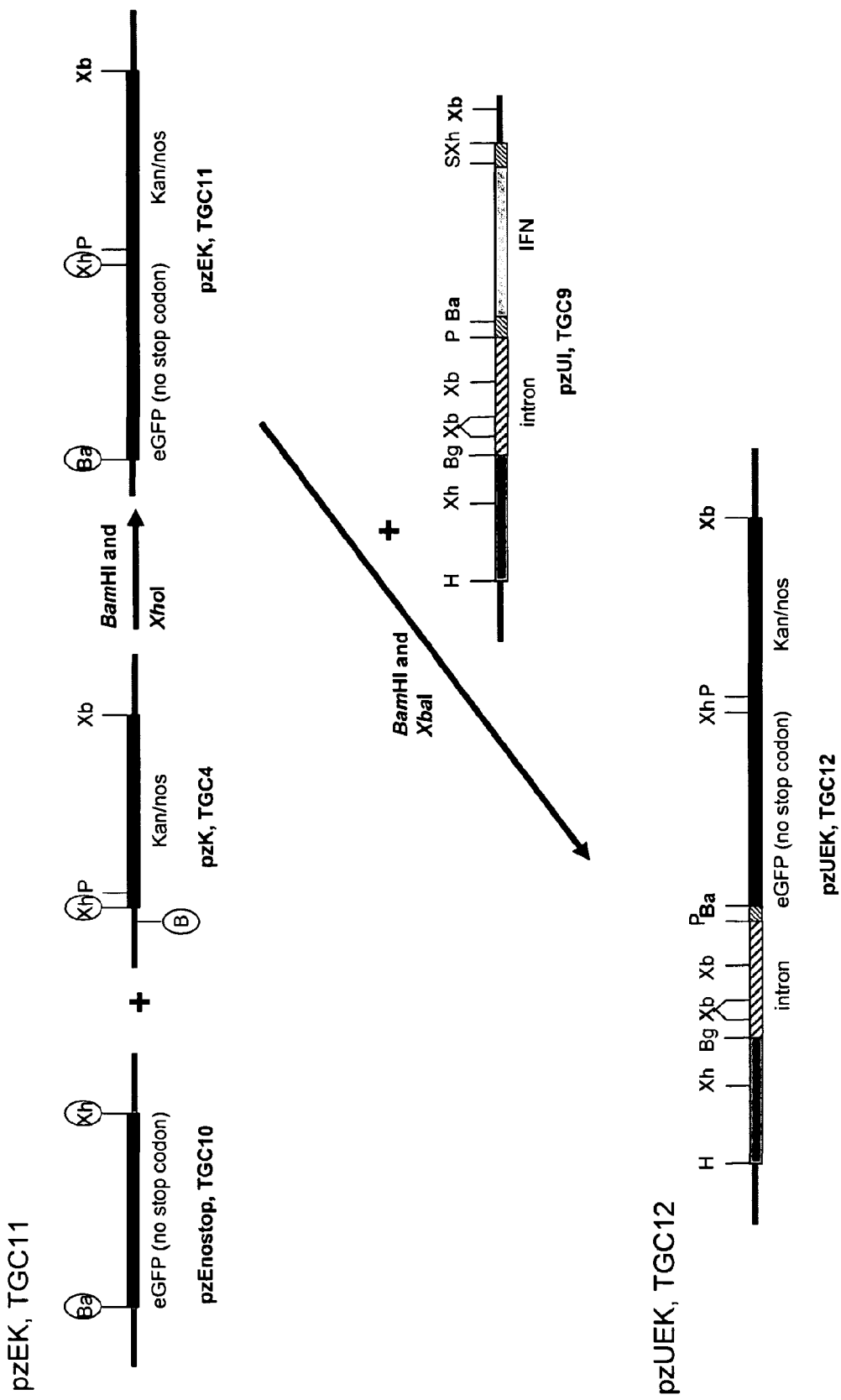

FIGS. 6A to 6B illustrate an exemplary set of constructs for producing a protein of interest from an Aloe plant. The plasmid constructions are labeled as pzUI (TGC9). TGC9 includes the full length ubiquitin promoter driving expression of human interferon alpha 2, and pzUEK (TGC12) (SEQ. ID. NO. 38), the full length ubiquitin promoter driving expression of a fusion protein containing eGFP (enhanced green fluorescent protein) (SEQ. ID. NO. 31) and the kanamycin resistance protein. The fusion protein combines the screening properties of both proteins (selection and visualization) in one.

As illustrated, the plasmid pzI (TGC8) was created by PCR amplification of the human interferon alpha 2 gene using PCR primers that each contain two distinct restriction enzyme sites (see Table I for primer sequence). The amplified interferon (IFN) gene has flanking 5' PstI and BamHI sites and 3' SacI and XhoI sites. The PCR generated IFN was then cloned as a PstI/XhoI fragment into the pZErO vector to create the construct pzI (TGC8) and introduce the BamHI and SacI sites for subsequent cloning. This construct contains the full-length IFN alpha gene and its signal sequence, responsible for directing the secretion of the IFN protein from the cell. This is depicted on Slide 3. These PCR generated clones were sequenced to confirm the absence of any DNA mutations.

As illustrated, the plasmid vector pzUI (TGC9) was created by cloning the IFN alpha 2 gene downstream of the full-length ubiquitin promoter. The PstI/XhoI fragment of IFN was released from pzI (TGC8) and ligated into pzU (TGC1) to create the construct pzUI (TGC9). This is depicted on Slide 3.

As illustrated, the eGFP gene was PCR amplified using a set of primers containing BamHI (5' end) and XhoI (3' end) restriction sites (see Table I for primer sequence). This PCR generated eGFP gene was created without a stop codon (to ultimately allow for expression of an eGFP-kan fusion protein). Thus translation does not terminate at the end of the eGFP sequence. The PCR amplified fragment was digested with restriction enzymes BamHI and XhoI and ligated into the BamHI and XhoI sites of pZErO, creating pzEnostop (TGC10). This is depicted on Slide 3. PCR generated clones were sequenced to confirm the absence of any DNA mutations.

As illustrated, pzEK (TGC11) generates a fusion construct between the eGFP gene and the kanamycin resistant gene. eGFP was released as a BamHI/XhoI fragment from pzEnostop (TGC10) and ligated into pzK (TGC4) to create the construct pzEK (TGC11). The eGFP gene is cloned in frame and 5' to kan/nos (SEQ. ID. NO. 35).

As illustrated, a BamHI/XbaI fragment from pzEK (TGC11) containing the eGFP/kan/nos cassette, was cloned into the BamHI and XbaI sites of pzUI (TGC9) in order to allow for expression of the eGFP/kan fusion gene. The IFN sequence is thus removed. This new construct, pzUEK (TGC12), expresses the eGFP/kan fusion protein from the full-length ubiquitin promoter (depicted in slide 4). This fusion protein retains the characteristics of each of the individual proteins, and thus has the obvious benefit of functioning both as visual marker and selective agent in one.

Figure 7A:
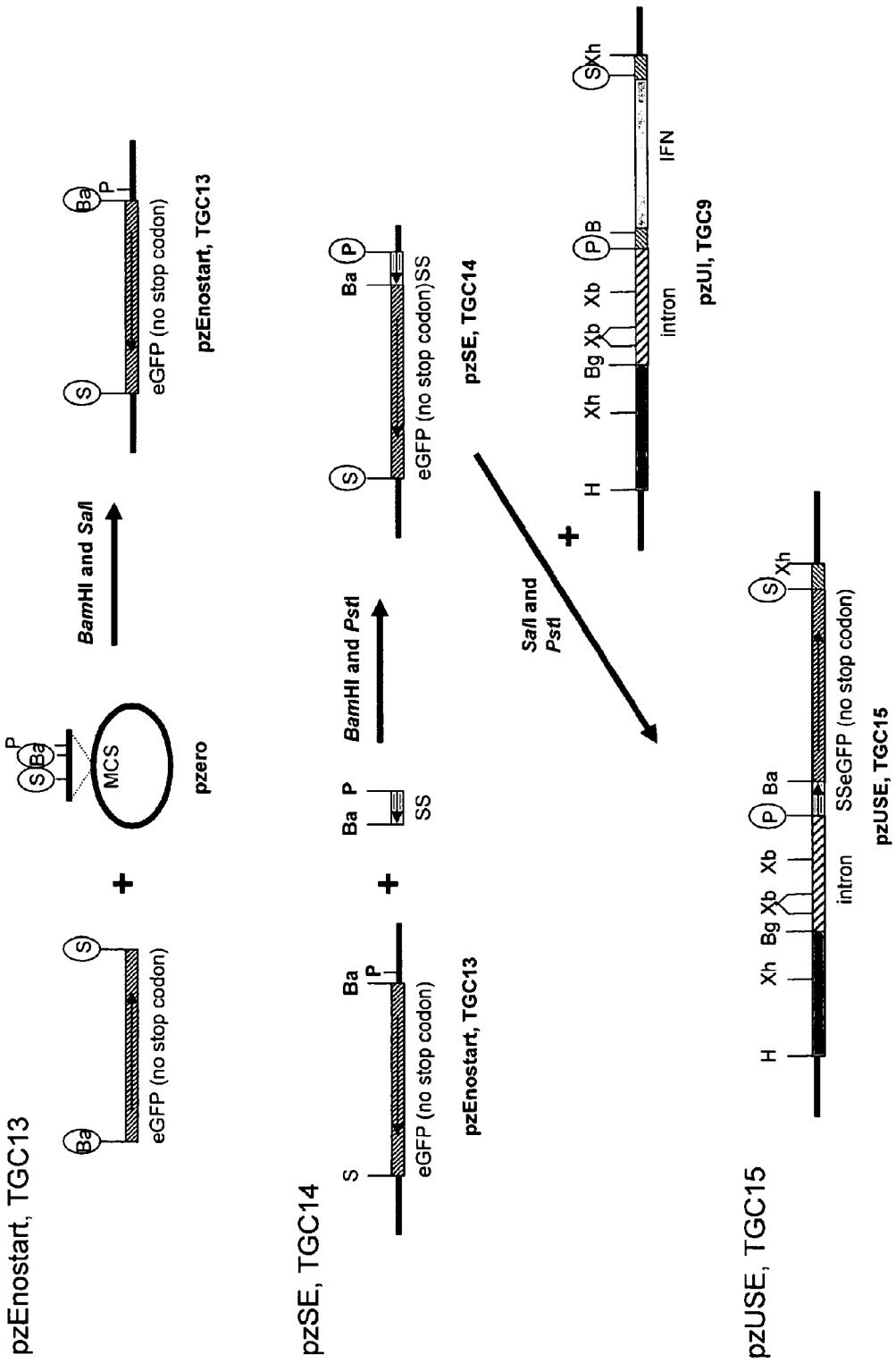
FIGS. 7A to 7C illustrate the construction of another plasmid vector system in accordance with aspects of the present inventions.
Figure 7B:
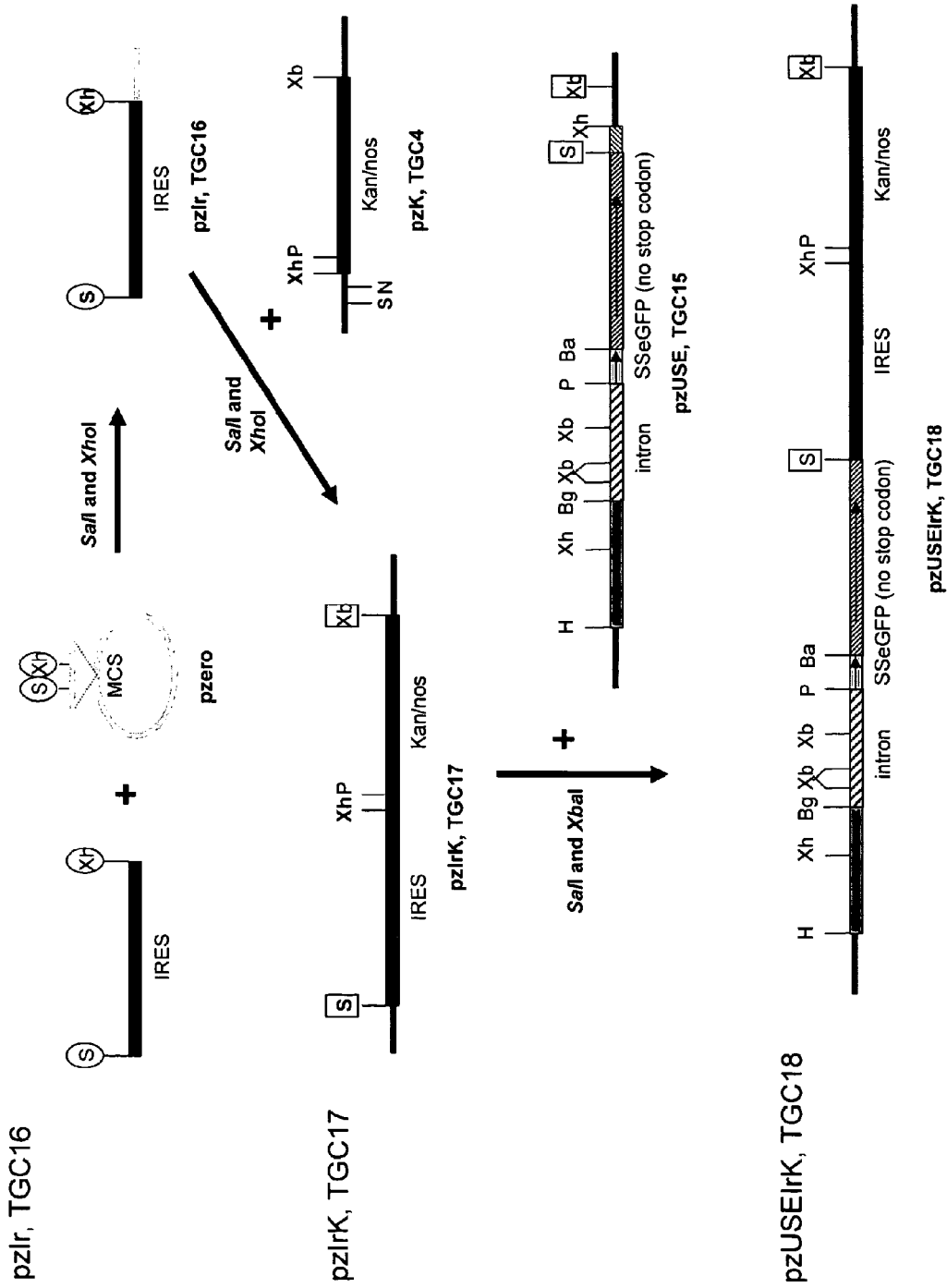
Figure 7C:
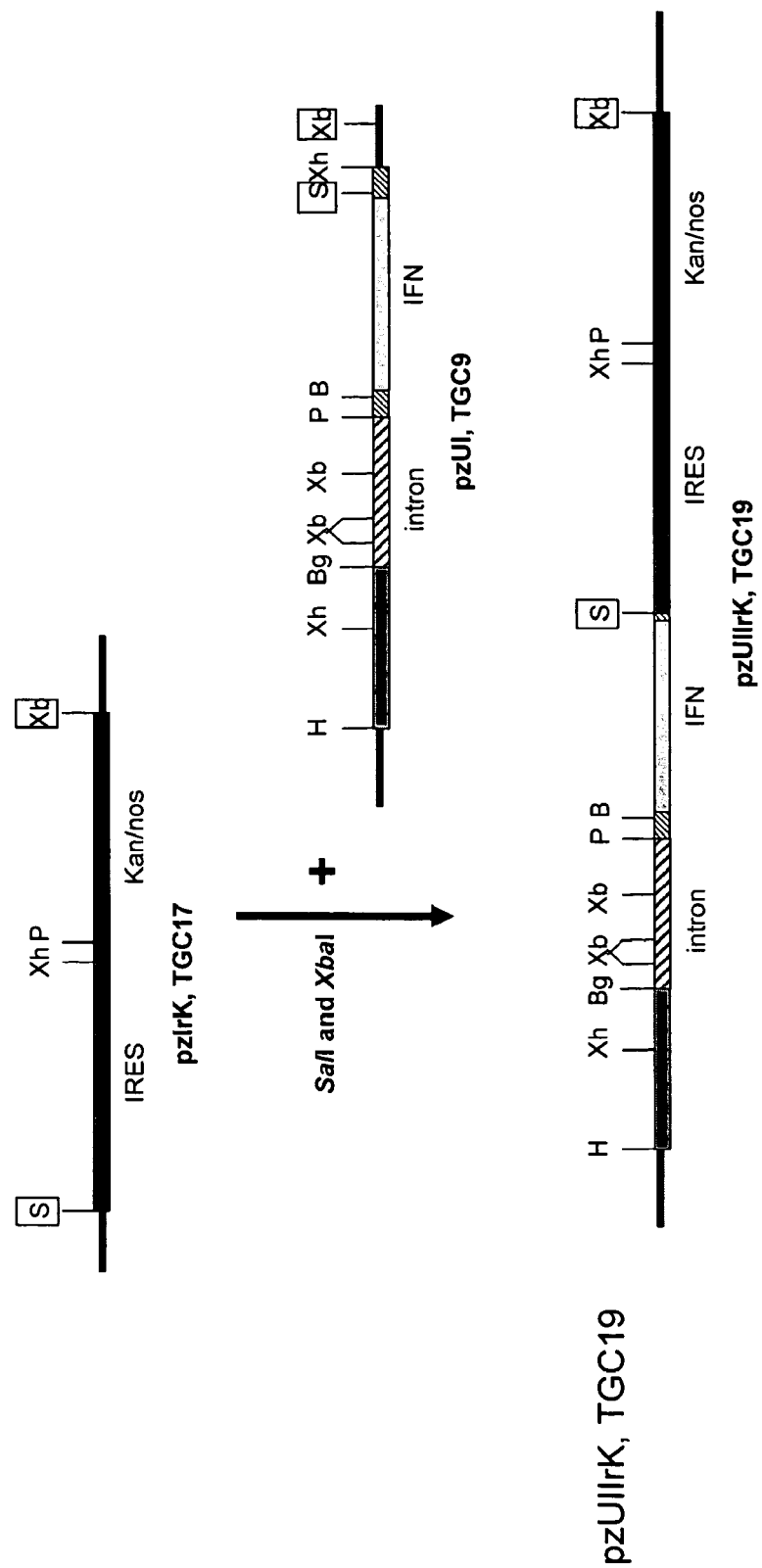

FIGS. 7A to 7C illustrate another exemplary set of constructs for producing a protein of interest from an Aloe plant. The illustrated vectors allow for the expression of two genes, as a single transcript, while still being translated into two distinct proteins. To accomplish this, the two genes are separated from one another by an intervening IRES element (internal ribosome entry sequence) (SEQ. ID. NO. 34). The IRES element provides a second, internal site, for ribosome attachment and translation. This second site allows for transcripts cloned 3' to the IRES element, to be separately translated. These vectors, namely pzUSEIrK (TGC18) (SEQ. ID. NO. 43) and pzUIIrK (TGC19) (SEQ. ID. NO. 39), were constructed in stages, ultimately allowing for the expression of eGFP or IFN (respectively) together with the kanamycin resistance marker.

As illustrated, the pzEnostart (TGC13) vector was created by first amplifying eGFP by PCR (table I for primer sequences) using primers containing the restriction enzyme sites BamHI (5' end) and SacI (3' end). This PCR product was cloned as a BamHI/SacI fragment into pZErO. The eGFP gene in this construct lacks an ATG translation start site, as this protein is expressed as a fusion with the alpha amylase signal sequence (see construction of pzSE, TGC14). This is depicted on Slide 5. These PCR generated clones were sequenced to confirm the absence of any DNA mutations.

As illustrated, the one strand of the signal sequence from the alpha amylase gene was synthesized and then made double stranded by fill in using PCR (table I for primer sequences). The signal sequence was then digested with the restriction enzymes PstI and BamHI and cloned into pzEnostart (TGC13). This is depicted on Slide 5. The signal sequence was cloned in frame, 5' to eGFP, and provides the translation initiation site for signal sequence eGFP fusion. Resulting pzSE (TGC14) clones were sequenced to confirm the absence of any DNA mutations.

As illustrated, the vector pzUSE (TGC15) was constructed to link the alpha amylase signal sequence (ss)-eGFP fusion with the ubiquitin promoter. The gene cassette containing the ss-eGFP from pzSE (TGC14) was cloned as a PstI/SacI fragment into pzUI (TGC9). This replaces the IFN gene cassette (released from pzUI (TGC9) by digesting with restriction enzymes PstI and SacI) creating pzUSE (TGC15). This is depicted on Slide 5.

As illustrated, the IRES element was amplified by PCR (table I for primer sequences) from pIRES2-EGFP (Clontech, BD Biosciences) with primers containing the restriction sites SacI (5' end) and XhoI (3' end). The amplified IRES element was cloned as a SacI/XhoI fragment into pZErO to create pzIr (TGC16). This is depicted on Slide 6. These PCR generated clones were sequenced to confirm the absence of any DNA mutations.

As illustrated, the IRES element from pzIr (TGC16) was then cloned as a SacI/XhoI fragment into pzK (TGC4) to create pzIrK (TGC17). Thus positioning the IRES upstream of the kan/nos gene cassette.

As illustrated, the IRES-kan-nos gene cassette was cloned as a SacI/XbaI fragment into pzUSE (TGC15) to create pzUSEIrK (TGC18). This is depicted on Slide 6. This construct expresses eGFP as a fusion with the alpha amylase signal sequence, targeting the eGFP for secretion from the cell. This makes it possible to visually monitor protein trafficking and accumulation within the transformed plant. This vector also expresses the kanamycin resistance protein (translated from the internal IRES element) and allows for selection in transgenic plants.

As illustrated, the IRES-kan/nos gene cassette was also cloned as a SacI/XbaI fragment into pzUI (TGC9) to create pzUIIrK (TGC19). This is depicted on Slide 7. This construct expresses IFN alpha 2 with a signal sequence for secretion. This vector also expresses the kanamycin resistance protein (translated from the internal IRES element) and allows for selection in transgenic plants. Both TGC18 and TGC19 express two genes as a single transcript, eliminating the need for a second promoter, and thus reducing the overall size of each vector. This is important as decreasing the overall size of transfected constructs increases the efficiency with which these elements are able to translocate to the nucleus, leading to stable integration and the selection of transgenic plants. A single promoter system also reduces the risk of disrupting flanking gene expression or other situations that might ultimately effect transgene expression.

The above listed plasmids may substitute other genes of interest for the interferon. As will be recognized by those skilled in the art, these may be substituted at the same locus or at other locations in the plasmids.

A prothrombin encoding sequence (SEQ. ID. NO. 36) may also be integrated into a plasmid vector in accordance with aspects of the present inventions as diagrammatically illustrated in FIG. 8. Prothrombin is the precursor protein to thrombin. It is cleaved at 2 sites by activated Factor X to release activated thrombin, a coagulation protein which converts soluble fibrinogen into insoluble strands of fibrin. The prothrombin gene cassette (1874 base pairs) was amplified using PCR primers (Table I for primer sequence). The eGFP gene cassette was released from pzUSEIrK (TGC18) vector by the restriction enzyme BamHI. The resulting 5' overhangs were subsequently removed with Mung Bean nuclease to create blunt ends. The blunt ends were dephosphorylated using calf intestinal phosphatase (CIP) by incubating at 50 degrees Celsius for 2 hrs, before ligating overnight with the prothrombin gene cassette at 15 degrees Celsius. This created pzUSTIrK (TGC20) (SEQ. ID. NO. 42). PCR generated clones were sequenced to confirm the absence of any DNA mutations.

A Dermcidin (DCD) encoding sequence (SEQ. ID NO. 30) may also be integrated into a plasmid vector in accordance with aspects of the present inventions as also diagrammatically illustrated in FIG. 8. Dermcidin was a recently reported broad spectrum antimicrobial peptide found constitutively expressed in the sweat glands. This protein is secreted into the sweat and transported to the epidermal surface. The PCR amplified DCD gene cassette has flanking BamHI restriction enzyme sites (Table I for primer sequence). The BamHI digested DCD gene cassette was ligated into the BamHI site of pzUSEIrK (TGC18) vector that used to be occupied by eGFP, creating pzUSDIrK (TGC21) vector (SEQ. ID. NO. 40). PCR generated clones were sequenced to confirm the absence of any DNA mutations.

A human Growth Hormone (hGH) encoding sequence (SEQ. ID. NO. 32) may also be integrated into a plasmid vector in accordance with aspects of the present inventions as also diagrammatically illustrated in FIG. 8. The hGH gene cassette was created by PCR amplification with flanking BamHI restriction enzyme sites (Table I for primer sequence). Then the BamHI digested hGH gene cassette was ligated into the BamHI site of pzUSEIrK (TGC18) vector that used to be occupied by eGFP, creating pzUSHIrK (TGC22) vector (SEQ. ID. NO. 41). PCR generated clones were sequenced to confirm the absence of any DNA mutations.

A human interferon gamma (hIFNg) encoding sequence may also be integrated into a plasmid vector in accordance with aspects of the present inventions as also diagrammatically illustrated in FIG. 8. The hIFNg gene cassette was created by PCR amplification with flanking BamHI restriction enzyme sites (Table I for primer sequence). The BamHI digested hIFNg gene cassette was then ligated into the BamHI site of pzUSEIrK (TGC18) vector that used to be occupied by eGFP, creating pzUSIfgIrK (TGC23) vector (SEQ. ID. NO. 37). PCR generated clones were sequenced to confirm the absence of any DNA mutations.

TABLE I

List of primer sequences used to create other expressed genes

| Primer name | Primer sequence | Sequence I.D. |
| --- | --- | --- |
| prothrombinF | AAACCATGGCGCACGTCCGAGGC | SEQ. ID. NO. 1 |
| prothrombinR | CTACTCTCCAAACTGATCAATGA | SEQ. ID. NO. 2 |
| dermcidinF | GGGGGATCCACCATGAGGTTCATGACTCTC | SEQ. ID. NO. 3 |
| dermcidinR | GGCGGATCCCTATAGTACTGAGTCAAGG | SEQ. ID. NO. 4 |
| hghF | GGGGGATCCACCATGGCTACAGGCTCCCGG | SEQ. ID. NO. 5 |
| hghR | GGCGGATCCCTAGAAGCCACAGCTGCCC | SEQ. ID. NO. 6 |
| hifngF | GGGGGATCCACCATGAAATATACAAGTTAT | SEQ. ID. NO. 7 |
| hifngR | TCCGGATCCTTAATAAATAGATTTAGA | SEQ. ID. NO. 8 |
| IFN pst-bam | CAACTGCAGGATCCAACAATGGCCTTGACCTTTGCTTTAC | SEQ. ID. NO. 9 |
| IFN sac-xho | CAACTCGAGCTCATTCCTTACTTCTAAACTTTCTTG | SEQ. ID. NO. 10 |
| eGFP bam [no start codon] | ATAGGATCCGTGAGCAAGGGCGAGGAGCTGTTC | SEQ. ID. NO. 11 |
| eGFP sac [no start codon] | TATGAGCTCTTACTTGTACAGCTCGTCCATGCC | SEQ. ID. NO. 12 |
| eGFP f bam [no stop codon] | CAGGGATCCACCATGGTGAGCAAGGGCGAGG | SEQ. ID. NO. 13 |
| eGFP r xho [no stop codon] | AGTCTCGAGCTTGTACAGCTCGTCCATGC | SEQ. ID. NO. 14 |
| Signal sequence AA pst bam | TATCTGCAGACCATGGTGAACAAACACTTCTTGTCCCTTTCGGTCCTCATCGTCCTCCTTGGCCTCTCCTCCAACTTGACAGCCGGGGATCC | SEQ. ID. NO. 15 |
| Signal sequence AA ss-pcr | GTGAATTCGGATCCCCCGGCTGTCAA | SEQ. ID. NO. 16 |
| IRES sac | ATTGAGCTCAAGCTTCGAATTCTGCAG | SEQ. ID. NO. 17 |
| IRES xho | ATACTCGAGGTGGCCATATTATCATCGTGTTTTTC | SEQ. ID. NO. 18 |
| kan xho | ATACTCGAGACCATGATTGAACAAGATGGATTGCAC | SEQ. ID. NO. 19 |
| Kan xba | ATTTCTAGACCAGAGCCGCCGCCAGCATTGACAGG | SEQ. ID. NO. 20 |
| prothrombinF | AAACCATGGCGCACGTCCGAGGC | SEQ. ID. NO. 21 |
| prothrombinR | CTACTCTCCAAACTGATCAATGA | SEQ. ID. NO. 22 |
| dermcidinF | GGGGGATCCACCATGAGGTTCATGACTCTC | SEQ. ID. NO. 23 |
| dermcidinR | GGCGGATCCCTATAGTACTGAGTCAAGG | SEQ. ID. NO. 24 |

TABLE I -continued

List of primer sequences used to create other expressed genes

| Primer name | Primer sequence | Sequence I.D. |
|---|---|---|
| hhghF | GGGGGATCCACCATGGCTACAGGCTCCCGG | SEQ. ID. NO. 25 |
| hghR | GGCGGATCCCTAGAAGCCACAGCTGCCC | SEQ. ID. NO. 26 |
| hifngF | GGGGGATCCACCATGAAATATACAAGTTAT | SEQ. ID. NO. 27 |
| hifngR | TCCGGATCCTTAATAAATAGATTTAGA | SEQ. ID. NO. 28 |

These sequences may contain their own signal sequence. Similar to the sequence in alpha interferon which was demonstrated as operable in an aloe plant, the native signal sequences within prothrombin, Dermcidin (DCD), human Growth Hormone (hGH), and human interferon gamma (hIFNg) may also be demonstrated to be functional in an aloe plant. Regardless, these protein encoding sequences may be cloned into a vector containing the alpha amylase signal sequence as illustrated examples of FIG. 8.

In the development of the above reference constructs, all vectors used for transformation were grown in 250 ml LB 50 ug/L zeocin and isolated using the CsCl method. The vectors were then used in transient transfection studies to ensure proper expression from each construct. Transfection using the gene gun was performed in maize, tobacco, and aloe, and expression monitored visually for expression of eGFP or by rt-PCR for expression of either IFN or kan.

Transformation

After the DNA constructs including the gene of interest and functional various function units incorporated into vectors are generated, the DNA constructs are introduced into the aloe cells using a number of techniques that will be recognized by those skilled in the art upon review of the present disclosure. These DNA constructs are generally designed to promote the formation of stably transformed aloe plants 10. Numerous methods for transforming plant cells with recombinant DNA are known in the art and may be used in the present inventions. Some methods for incorporation of DNA constructs contained in vectors into aloe cells or tissues to create stable aloe transformants can include infection with *A. tumefaciens* or *A. rhizogenes*, infection with replication deficient viruses, biolistic transformation, protoplast transformation, gene transfer into pollen, injection into reproductive organs, injection into immature embryos, or similar methods. Currently, two of the more commonly used methods for plant transformation are *Agrobacterium*-mediated transformation and biolistic transformation. Transformed aloe cells or callus tissues are typically grown in appropriate nutrient medium to select for transformed cells. Frequently, a selection medium includes a toxin or other selecting factor that kills non-transformed cells. Various medium changes will allow the production of aloe plants 10 that contain the gene of interest as will be recognized by those skilled in the art upon review of the present disclosure.

In the practice of transformation DNA is typically introduced into only a small percentage of target plant cells in any one transformation experiment. Marker genes are used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the herbicides to which plants of this inventions may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar orpat) and glyphosate (aroA or EPSPS). Examples of such selectable are illustrated in U.S. Pat. Nos. 5,550,318; 5,633,435; 5,780,708 and 6,118,047, all of which are incorporated herein by reference. Selectable markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

In general it is useful to introduce recombinant DNA randomly, i.e. at a non-specific location, in the genome of a target plant line. In special cases it may be useful to target recombinant DNA insertion in order to achieve site-specific integration, for example to replace an existing gene in the genome, to use an existing promoter in the plant genome, or to insert a recombinant polynucleotide at a predetermined site known to be active for gene expression. Several site specific recombination systems exist which are known to function implants include cre-lox as disclosed in U.S. Pat. No. 4,959,317 and FLP-FRT as disclosed in U.S. Pat. No. 5,527,695, both are incorporated herein by reference and are discussed in more detail below.

For *Agrobacterium tumefaciens* based plant transformation system, additional elements present on transformation constructs will include T-DNA left and right border sequences to facilitate incorporation of the recombinant polynucleotide into the plant genome. With infection with *agrobacterium* (*A. tumefaciens*), aloe callus tissue is incubated for 1 hour at room temperature with an overnight culture of *agrobacterium* including the vector incorporating the DNA construct. The *Agrobacterium* is grown in appropriate selection medium. The selection medium typically includes streptomycin and kanamycin. The selection medium may also contain acetosyringone. The acetosyringone at a concentration of 50 uM to 250 uM typically increases the efficiency of monocot infectivity. After growth on the selection media, infected aloe tissue may be transferred to media in Petri dishes with no selection for two (2) days in the dark 25 degrees Celsius. An exemplary suitable medium could be MS media with acetosyringone. Cefotaxime may then be added for two (2) days to kill the *agrobacterium*. Cells are then replated on media containing 50 mg/L Kanamycin to select for transformed aloe cells and shoot inducing growth factors (0.2 mg/L NAA, 2 mg/L BAP) for four (4) weeks, 16 hrs light.

Regenerating shoots may then transferred to rooting medium (½ MS with 0.2 mg/L NAA) to develop roots (after about 4 to 6 weeks) before being transferred to soil.

With biolistic transformation, aloe cells or callus tissue are bombarded directly with the vector construct. Various embodiments and aspects of biolistic transformation are disclosed in U.S. Pat. No. 5,015,580 (soybean); U.S Pat. No. 5,550,318 (corn); U.S. Pat. No. 5,538,880 (corn); U.S. Pat. No. 5,914,451 (soybean); U.S. Pat. No. 6,160,208 (corn); U.S. Pat No. 6,399,861 (corn) and U.S. Pat. No. 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. Further, a variety of biolistic transformation apparatus may be use such as for example a Biolistic PDS-1000/He particle delivery system from Bio-Rad, Inc. In this approach, the vector and associated DNA construct may be bound to gold or other particles and fired directly into the aloe cells. The bombarded aloe cells are grown without selection for 4 days in the dark before being transferred to selection media. Again, the selection media may include 50 mg/L Kanamycin. Transformants typically begin to form within 8-12 weeks and can be transferred to shooting and rooting media for a further 8-12 weeks. Once roots have begun to form, plantlets can be transferred to soil.

Transformation can also be achieved using a variety of other techniques. Such techniques include viral infection using replication compromised viral vector systems, electroporation particularly of callus cells or protoplasts grown in liquid culture, and PEG or lipid mediated transfer into protoplasts. The selection for transformants could then follow the same basic steps as that outlined for biolistic transformation.

Figure 3:
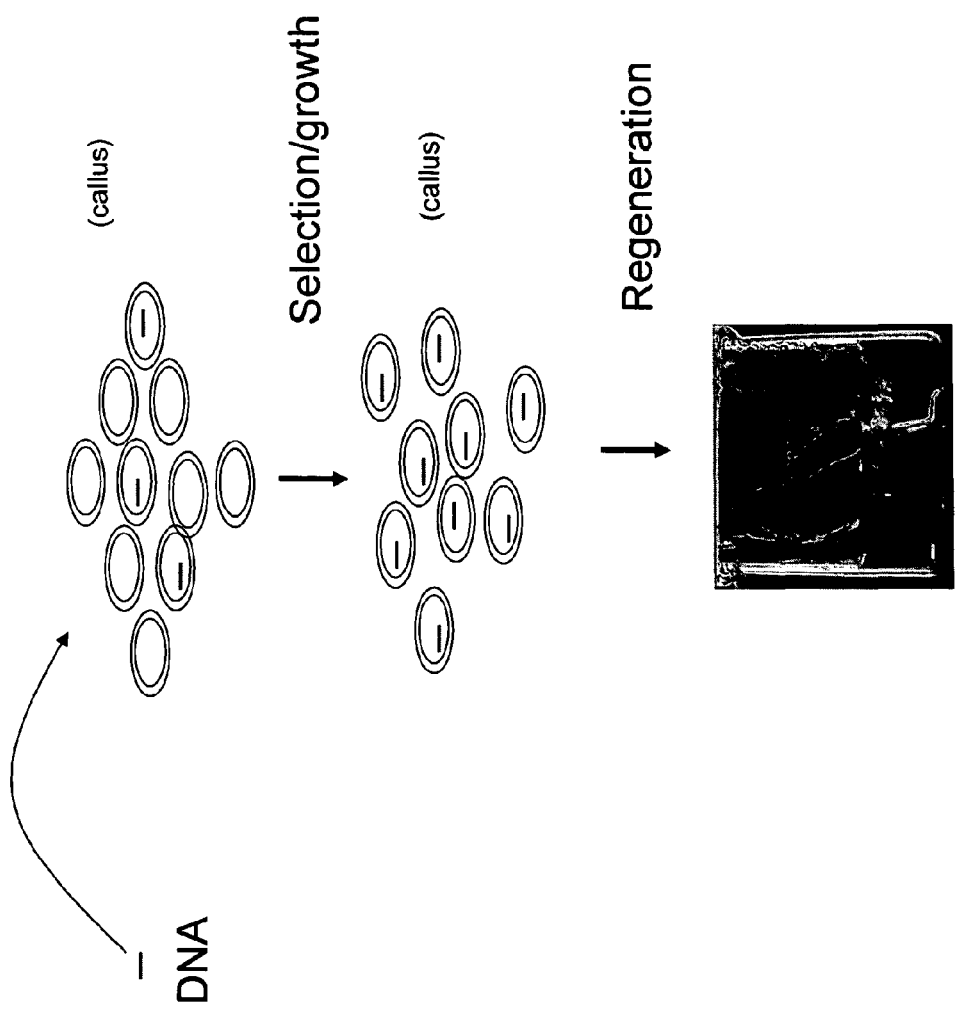
FIG. 3 diagrammatically outlines various steps for generating a transgenic aloe plant.
Figure 4:
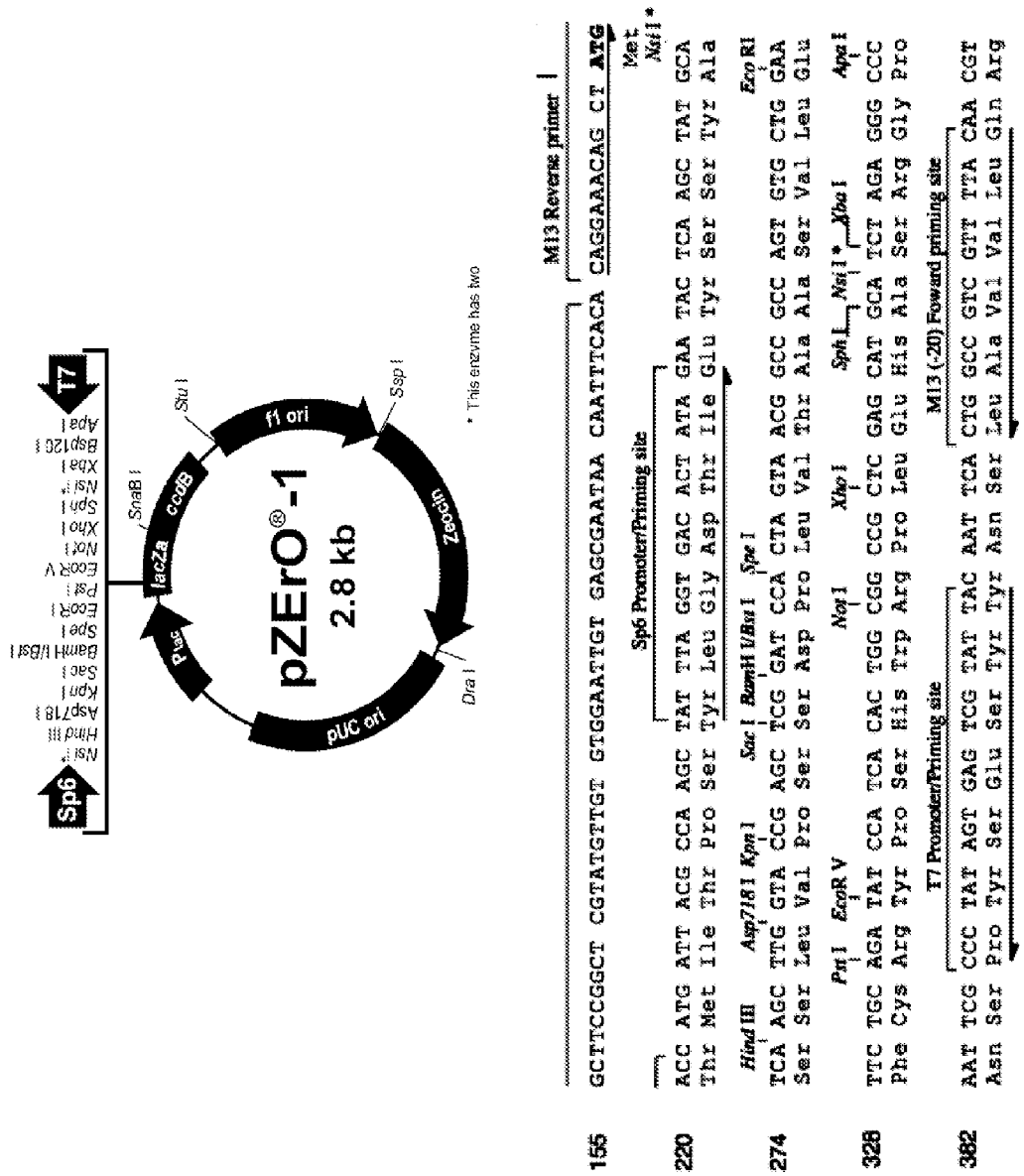
FIG. 4 diagrammatically illustrates components of a plasmid vector including sequence information (DNA sequence disclosed as SEQ ID NO: 45 and protein sequence disclosed as SEQ ID NO: 46)

Once introduced into the aloe callus tissues, constructs may be incorporated into the plant genetic material as is generally illustrated in FIG. 3. In other aspects, the constructs may be stably integrated into the cell outside of the Aloe plants 10 genetic material. Depending on the construct, the protein of interest may or may not be expressed absent some form of induction of transcription. In one aspect, constructs once introduced into Aloe cells may direct protein synthesis or transport to specific tissues of the Aloe plant 10. Typically, this occurs when a targeting signal sequence is included on the protein of interest.

Site Specific Integration (Cre-Lox)

In one aspect, the present inventions may utilize site-specific integration or excision of DNA constructs introduced into an aloe plant. An advantage of site-specific integration or excision is that it can be used to overcome problems associated with conventional transformation techniques, in which transformation constructs typically randomly integrate into a host genome in multiple copies. This random insertion of introduced DNA into the genome of host cells can be lethal if the foreign DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the DNA constructs inserted into the transgenic aloe plant's 10 genome, often only desiring the insertion of a single copy of the DNA construct.

Site-specific integration or excision of transgenes or parts of transgenes can be achieved in plants by means of homologous recombination (see, for example, U.S. Pat. No. 5,527, 695, specifically incorporated herein by reference in its entirety). Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases.

Introduced DNA sequences can be targeted via homologous recombination by linking a DNA molecule of interest to sequences sharing homology with endogenous sequences of the host cell. Once the DNA enters the aloe cell, the two homologous sequences can interact to insert the introduced DNA at the site where the homologous genomic DNA sequences were located. Therefore, the choice of homologous sequences contained on the introduced DNA will determine the site where the introduced DNA is integrated via homologous recombination. For example, if the DNA sequence of interest is linked to DNA sequences sharing homology to a single copy gene of a host aloe cell, the DNA sequence of interest will be inserted via homologous recombination at only that single specific site. However, if the DNA sequence of interest is linked to DNA sequences sharing homology to a multicopy gene of the host eukaryotic cell, then the DNA sequence of interest can be inserted via homologous recombination at each of the specific sites where a copy of the gene is located.

DNA can be inserted into the host genome by a homologous recombination reaction involving either a single reciprocal recombination (resulting in the insertion of the entire length of the introduced DNA) or through a double reciprocal recombination (resulting in the insertion of only the DNA located between the two recombination events). For example, if one wishes to insert a foreign gene into the genomic site where a selected gene is located, the introduced DNA should contain sequences homologous to the selected gene. A single homologous recombination event would then result in the entire introduced DNA sequence being inserted into the selected gene. Alternatively, a double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus, only those DNA sequences located between the two regions sharing genomic homology become integrated into the genome.

Although introduced DNA sequences can be targeted for insertion into a specific genomic site via homologous recombination, in higher eukaryotes homologous recombination is a relatively rare event compared to random insertion events. In aloe cells, foreign DNA molecules find homologous sequences in the aloe plant's genome and recombine at a frequency of approximately $0.5\text{-}4.2$ times $10^{-4}$. Thus any transformed cell that contains an introduced DNA sequence integrated via homologous recombination will also likely contain numerous copies of randomly integrated introduced DNA sequences. One way of avoiding these random insertions is to utilize a site-specific recombinase system. In general, a site specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

A number of different site specific recombinase systems could be employed in accordance with the instant inventions, including, but not limited to, the Cre/lox system of bacteriophage P1 (U.S. Pat. No. 5,658,772, specifically incorporated herein by reference in its entirety), the FLP/FRT system of yeast (Golic and Lindquist, 1989), the Gin recombinase of phage Mu (Maeser and Kahmann, 1991), the Pin recombinase of *E. coli* (Enomoto et al., 1983), and the R/RS system of the pSR1 plasmid (Araki et al., 1992). The bacteriophage P1 Cre/lox and the yeast FLP/FRT systems constitute two particularly useful systems for site specific integration or excision of transgenes. In these systems, a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors.

FIG. 8 illustrates a particular exemplary protocol using a Flp/Frt and Cre/Loxp recombinase system. In such a system, site-specific recombinases from bacteriophage and yeasts may be used as tools to manipulate DNA both in the test-tube and in living organisms. Recombinases/recombination site combinations include Cre-Lox, FLP-FRT, and R-RS, where Cre, FLP and R are recombinases, and Lox, FRT, and RS are the recombination sites. To use this system, a transgenic plant containing the specific sites for recombination is generated. A parent transgenic aloe plant 10 is created by transfecting a vector, expressing a selectable marker and engineered to contain Frt and Lox sites in tandem. Both the Frt and Lox sites consist of three elements, a spacer sequence of eight (8) nucleotides between two (2) inverted repeats of thirteen (13) nucleotides each. The inverted repeats serve as the DNA binding domain for the specific recombinase while the spacer element is variable but essential for homologous recombination. By altering the spacer element of either the LoxP or FRT sites, multiple distinct sites for recombination can be created. By alternating Frt and Lox sites a system allowing multiple site directed integrations can be created (as outlined in FIG. 8). This system may have a number of advantages. Disruption of endogenous genes is minimized after the generation of the initial parent plant. The efficiency of transformation is increased by the expression of site specific recombinases. Using the lox and frt sites in tandem allows for the selective removal of selection markers while retaining the gene of interest. And once a parent plant has been created cellular propagation and regenerative potential is enhanced. The parent plant however is the first step and is created following standard transformation methods (biolistics or *Agrobacterium*). Subsequent transgenic plants are created by co-transfection of a vector containing both a LoxP and Frt site as well as the gene of interest and a selectable marker, together with a vector expressing the Cre recombinase. Expression of the Cre recombinase induces homologous recombination through the LoxP sites of the vector and the parent plant. Transformants are selected by expression of selectable markers and induced to regenerate. Subsequent transformation with a vector expressing Flp recombinase can remove the selectable marker and allow for subsequent integration into other Loxp sites.

Production of Viable Plant

Following transformation of Aloe cells or Aloe tissues, the transformed Aloe cells or Aloe tissues may be grown into plantlets. Aloe cells that survive exposure to the selective agent, or aloe cells that have been scored positive in a screening assay, may be cultured in regeneration media and allowed to mature into transgenic aloe plants 10. Developing aloe plantlets regenerated from transformed aloe cells can be transferred to plant growth mix, and hardened off, for example, in an environmentally controlled chamber at about 85% relative humidity, 600 ppm $CO_2$, and 25-250 microeinsteins $m^{-2}s^{-1}$ of light, prior to transfer to a greenhouse or growth chamber for maturation. The transformed aloe plants 10 are regenerated from about 6 weeks to 10 months after a transformant is identified, depending on the initial tissue. The regenerated transformed aloe plant 10 or its progeny seed or plants can typically be tested for expression of the recombinant DNA.

Regenerating a transgenic aloe plant 10 from transformed undifferentiated callus tissue or meristem tissue involves primarily manipulating the growth factors auxin and kinetin. The first step is to promote shoot growth. Shoot inducing medium typically contains a low concentration of auxin (0.2 mg/L NAA) and a relatively high concentration of cytokinin (2 mg/L BAP). Reduced sugar concentration to 2% sucrose (which affects the osmotic pressure) can also help in plant regeneration. Cells on shooting medium are placed in incubators at 25° C. with a 12 hr/day light cycle. Shoots that begin to form are excised from the primary callus after they reach a length of roughly 2 cm and placed in rooting medium. These shoots can also be maintained in shooting medium to encourage the development of further shoots. Rooting medium promotes root development and typically contains ½ MS medium and a relatively low concentration of auxin (0.2 mg/L NAA). After roots begin to develop (1-2 cm) the plantlets can be transferred to soil and acclimatized by gradually reducing the relative humidity. Once generated, the transgenic aloe plants 10 may be propagated by seed, clonal propagation methods, or otherwise as will be recognized by those skilled in the art upon review of the present disclosure.

Extraction and Purification of Proteins from Plants or Plant Cells

The structural proteins or enzymes introduced via vectors into plant cells and plants may be found in various tissues of the Aloe plant 10 including roots, tubers, leaves, seeds, flowers, sap or in a combination of plant parts and developmental stages. In one aspect, the protein or proteins of interests are concentrated in the gelatinous matrix in the central portion of the leaf. In another aspect, the protein or proteins of interest are biologically active and provide some degree of medicinal effect when extracted from the Aloe leaf 12. In another aspect, the protein or proteins of interest and the at least one native aloe protein, carbohydrate and/or other compound found of the gelatinous matrix act synergistically to provide a desired treatment for a patient. Protein extraction can be from total biomass or a particular tissue. Protein extraction from plant cells may include physical and chemical methods. Protein extraction from leaves or sap may involve filtration, ultracentrifugation, chemical extraction and affinity chromatography.

In one aspect, the protein of interest may accumulate within the gel of the leaf of the transformed aloe plant 10. This region is primarily water, roughly 99%, and free of harmful proteases. Extraction of the gel is an established technique that will be understood by those skilled in the art. Some of the proteins, particularly cosmetic, may be used to supplement the aloe gel directly and may never need to be individually isolated from the gel.

EXAMPLES

Methodologies for Isolation of Plant Cells

In a first example, shoot meristem tissue for direct use or for callus initiation is isolated from the stalk of the aloe, either *Aloe vera*, *Aloe ferox* or *Aloe arborescence*. The leaf sections are removed and the stalk is cut laterally through the longitudinal axis of the aloe leaf. Tissue is sterilized with a mixture of Tween 20 (0.05%) and hypochlorite (5%) for 10 min, followed by 30 seconds ethanol, rinse 3× sterile water. Sections are then plated with the exposed surface lying sideways to the plate in MS media with agar (0.8-1%) containing various concentrations of the growth factors, auxin and cytokinin, and 2-3% sucrose. Growth conditions vary depending on the desired process. Callus culture without shoot development is typically initiated by growing these sections in NAA (2-5 mg/L) without BAP or with low concentration of BAP (0.2 mg/L). Undifferentiated cells begin to grow along the areas of the cut stalk and can be subcultured and maintained on separate dishes. Shoot induction can be initiated directly by placing such fragments in shooting medium—MS media containing 0.2 mg/L NAA (or IAA 0.2 mg/L) and 2 mg/L BAP. Both NAA and IAA work as a source of auxin and there is a range of concentrations of both auxins and cytokinins that have effect. Callus cells from immature embryos are developed from commercially available seeds. The seeds are first sterilized (ethanol 30 sec, 5% hypochlorite plus 0.05% Tween 20 for 15 min and rinsed 3× in sterile water). Sterilized seeds are then left overnight at 4 degrees Celsius in water. The immature embryo is isolated by removing the seed coat. A small cut is made at one corner of the triangular shaped seed and the embryo is squeezed out. This is then plated on MS media containing either auxin alone (NAA 2-5 mg/L) to induce callus, or auxin and cytokinin (NAA 0.2 mg/L, BAP 2 mg/L) to induce callus and shoot propagation. Sugar concentration is typically 2-3%.

Callus cells from the shoot apical meristem are developed from a one to two centimeter segment cut from the base of the young aloe plant 10 with all the leaves removed. The fragment is surface sterilized and replated in 1% agar with MS media and auxin and cytokinin (2 mg/L NAA 0.2 mg/L BAP).

Callus cell induction initiates within 1-2 weeks. Cells can then be isolated from these cultures and used as starting material for transformation.

DNA Constructs i. pBI121 Ubiquitin Interferon Vector (pBI-UI).

The pBI121 *Agrobacterium* binary vector was used as the backbone for the creation of pBI-UI. The human interferon alpha 2 gene with signal sequence was amplified from human 293 cells using gene specific primers containing 5' PstI and 3' SacI/XhoI restriction sites. The 587 bp interferon PCR product was cloned into pZErO and sequenced. The 1962 bp ubiquitin (Ubi) promoter element from maize was also cloned into pZErO by amplifying the region from the vector pUBI-GFP and cloning into 5' HindIII and 3' PstI restriction sites. The Ubi fragment was then subcloned into the pZero interferon vector using HindIII/PstI (pZErO UI). The intact Ubi interferon cassette was then subcloned into pBI121 using HindIII/SacI and removing the CaMV 35S promoter and GUS gene resulting in pBI UI. This vector retains the right and left T-element border regions necessary for *agrobacterium* mediated infection and transformation and expresses the kanamycin resistance gene (NPTII) under the control of the Nos promoter.

ii. pZErO Ubiquitin Interferon IRES Kanamycin. (pZ UIIK).

This vector was created by cloning the Ubi promoter into the pZErO cloning vector. Behind this fragment was cloned a cassette containing human interferon alpha 2 together with an IRES (internal ribosomal entry sequence) and the kanamycin resistance gene. This unit is expressed as a single transcript but translated as two distinct proteins (due to the second translational initiation site provided by the IRES). This allows both the selectable marker and interferon to be expressed under the control of the Ubi promoter.

iii. The Double Plasmid System Employing Cre and Flp Recombinases.

A parent plant is first generated which expresses the selectable marker having the cre and flp sites for targeted integration. A secondary transfection introducing vectors with genes of interest is targeted to the cre sites. Unwanted genetic material is then removed using flp.

Introduction of DNA Constructs into Isolated Plant Cells i. *Agrobacterium* Mediated Gene Transfer.

The *Agrobacterium* strain LB4404 (Invitrogen, Carlsbad, Calif.) was electroporated with the pBI UI vector and positive clones selected on LB agar plates containing 50 ug/ml kanamycin and 100 ug/ml streptomycin. Individual clones were grown overnight at 30 degrees Celsius in LB media containing 250 uM acetosyringone. Infection took place by submerging plant fragments or callus in the overnight cultures, blotting dry on sterile filter paper, and plating on MS agar plates containing 250 uM acetosyringone at 25 degrees Celsius in the dark. Two days after infection, tissue was transferred to MS agar plates containing 200 uM cefotaxime to kill the *Agrobacterium*. The tissue is then transferred to MS agar plates containing 50 mg/L kanamycin and 0.2 mg/L NAA and 2 mg/L BAP to select for transformants and induce shoot regeneration. The tissue is grown in 12 hours light at 25 degrees Celsius. Adventitious shoots are grown until they reach roughly 2 cm in length before they are excised and replanted on rooting media with continued selection. Plantlets expressing genes of interest are assayed for expression levels and transferred to soil.

ii. Biolistic Gene Transfer.

Gold particles (0.6-1 um) are coated with the vector including the DNA construct. The gold particles are washed 15 minutes in 70% ethanol by vortexing and soaking, followed by 3 washes in sterile water. The gold particles are then resuspended in 50% glycerol to a concentration of 60 mg/ml. To coat vector DNA on the washed particles, 3 mg of particles are added to a 1.5 ml microfuge tube. To this is added 5 ul DNA at a concentration of 1 ug/ul, 50 ul 2.5M CaCl2, and 20 ul 0.1 M spermidine, and vortexed for 2-3 min. This is allowed to settle, spun for 1-2 sec and the liquid removed. To this is added 140 ul of 70% ethanol, spun, and the liquid discarded. To this is added 140 ul 100% ethanol, spun and the liquid discarded. To the precipitate is added 48 ul 100% ethanol and gently resuspended. The gene gun apparatus (PDS 1000/He, Bio-Rad Laboratories, Inc., Hercules, Calif.) is sterilized using 70% ethanol. The gene gun apparatus was assembled using the shortest gap distance between the macrocarrier holder and stopping screen (recommended setting). Coated gold particles (8 ul) are pipetted onto the center of the macrocarriers. The target distance was set depending upon the target tissue (6 cm tissue, 9 cm callus) with a rupture disk of 600-1100 psi.

In a first example, following bombardment cells were plated on MS agar plates containing 2 mg/L NAA without selection for 1 week in the dark at 25 degrees Celsius. Cells were then transferred to MS agar plates containing 50 mg/L kanamycin for selection and auxin (2 mg/L NAA) and cytokinin (0.2 mg/L, 6-benzylaminopurine) for 4-5 more weeks. The cells are grown for 12 hours in light at 25 degrees Celsius.

In a second example, microprojectile bombardment was carried out on a plate of MS (4 g/L MS salts, 1 mg/L (1000×) MS vitamin stock, 2 mg/L NAA, 100 mg/L myo-inositol, 2.76 g/L proline, 30 g/L sucrose, 100 mg/L casein hydrolysate, 36.4 g/L sorbitol, 36.4 g/L mannitol, 2.5 g/L gelrite, pH 5.8). The bombarded callus was left on MSOSM for 1 hour after bombardment and then transferred to MS initiation medium (4 g/L MS salts, 1 mg/L (1000×) MS vitamin stock, 2 mg/L NAA, 100 mg/L myo-inositol, 2 g/L proline, 30 g/L sucrose, 100 mg/L casein hydrolysate, 2.5 g/L gelrite, pH 5.8). After 7-10 days on MS, the bombarded callus was transferred to MSS selection medium (4 g/L MS salts, 1 mg/L (1000×) MS vitamin stock, 2 mg/L NAA, 100 mg/L myo-inositol, 30 g/L sucrose, 2.5 g/L gelrite, pH 5.8) with 50 mg/L kanamycin for selection of transformed cells. After 3 weeks, individual callus pieces were transferred to fresh MSS medium. Within 6-8 weeks of bombardment, kanamycin resistant clones emerged from selected callus pieces.

iii. Protoplast.

Protoplasts are plant cells lacking their outer cell wall. The advantage of creating these cells is to increase the efficiency of transfection and such cells are able to fuse together forming a somatic cell hybrid. Somatic cell hybrids could mix up the genes from different plants potentially arriving at something completely new.

The technique for using protoplasts in accordance with the present inventions may include growing the cells in liquid culture (2-3 days in logarithmic growth phase). The cells are then spun down (1000× Gravity for 5 min). The cells are resuspended in a solution containing cellulase, macerozyme, and pectolyase. Shake over night at 25 degrees Celsius in the dark. Centrifuge (600× Gravity for 5 min.) and remove the supernatant. The protoplasts are resuspended in culture medium and spun one more time to remove traces of enzymes. The protoplasts cannot be stored or propagated and must be used for transfection or somatic cell fusion relatively quickly.

Production of Viable Plants Containing DNA Constructs

In a first example, successful transformants are selected initially for their resistance to cellular toxins, e.g. kanamycin. Stably transfected cells must express both the resistance marker and the gene of interest, such as for example a gene encoding interferon, as well to be able to regenerate the intact plant. 50 mg/L kanamycin is added to the MS agar plates to initiate selection. The course of selection depends in part on the speed with which the cells replicate but can take between 6 to 10 weeks. During this time transformed tissue is induced to regenerate by adding 0.2 mg/L NAA and 2 mg/L BAP to the MS agar plates and encouraging shoot development with a 12 hr/day light cycle (with continued selection pressure). As adventitious shoots begin to develop they can be assayed for gene expression at about 2 cm in length. Shoots expressing desired gene products (as assayed by RT-PCR, Western blot, and biological assay) are subsequently transferred to MS agar plates to induce root formation (½ MS plus 0.2 mg/L NAA).

In a second example, regeneration of transgenic callus is accomplished by transferring about 15 small pieces (approximately 4 mm) to Regeneration Medium I (4.3 g/L MS salts, 1 ml/L (1000×) MS vitamin stock, 100 mg/L myo-inositol, 60 g/L sucrose, 3 g/L gelrite, pH 5.8) with added filter sterilized kanamycin (50 mg/L) and incubating for 2-3 weeks at 25 degrees Celsius in the dark. Matured somatic embryos are transferred to the light on Regeneration Medium II for germination (4.3 g/L MS salts, 1 ml/L (1000×) MS vitamin stock, 100 mg/L myo-inositol, 30 g/L sucrose, 3 g/L gelrite, pH 5.8) with added filter sterilized kanamycin (50 mg/L).

What is claimed is:

1. A transgenic aloe cell comprising a recombinant DNA construct, said construct comprising a promoter, a sequence encoding an exogenous protein, a termination sequence, and a translocation sequence encoding a secretion signal peptide,
   wherein the promoter is an ubiquitin promoter from maize having SEQ ID NO. 44;
   wherein the exogenous protein is expressed from the DNA construct, and said aloe cell is a species selected from the group consisting of *Aloe vera*, Aloe ferox and Aloe arboresence.

2. The transgenic aloe cell of claim 1, wherein said exogenous protein is a mammalian protein selected from the group consisting of interferons, immunoglobulins, lymphokines, growth factors, hormones, blood factors, and histocompatibility antigens.

3. The transgenic aloe cell of claim 1, wherein said recombinant DNA construct has at least one enhancer element.

4. The transgenic aloe cell of claim 1, wherein said recombinant DNA construct has at least one selectable marker gene conferring resistance to a compound chosen from the group consisting of kanamycin, chloramphenicol, G418, hygromycin B, paromomycin, glufosinate, glypho sate and gentamycin.

5. A transgenic aloe plant regenerated from the transgenic aloe cell of claim 1.

6. A method for producing an exogenous protein in Aloe cells, said method comprising:
   providing transgenic Aloe cells selected from the group consisting of *Aloe vera, Aloe ferox* and *Aloe arboresence*, wherein said transgenic Aloe cells comprise a recombinant DNA construct comprising a promoter, a sequence encoding the exogenous protein, a termination sequence and a translocation sequence encoding a secretion signal peptide;
   wherein the promoter is an ubiquitin promoter from maize having SEQ ID NO. 44;
   cultivating the cells so that at least a portion of the exogenous protein encoded by the DNA construct is expressed by the cells, and isolating the expressed exogenous protein.

7. The method of claim 6, wherein said exogenous protein is a mammalian protein selected from α-interferon, γ-interferon, prothrombin, dermicidin and human growth hormone.

8. The method of claim 6, wherein said translocation sequence is the alpha amylase secretory sequence from rice (Oryza sativa).

9. The method of claim 6, wherein the transgenic Aloe cells are generated by a process comprising:
   isolating aloe cells from an aloe seed, aloe meristem tissue or an aloe plant;
   growing the aloe cells in culture in a nutrient medium containing an auxin and a cytokinin to form a callus;
   transforming the callus with the recombinant DNA construct; and
   selecting for transformed aloe cells containing the recombinant DNA construct while growing the callus in culture medium.

10. The method of claim 6, wherein said exogenous protein is a mammalian protein selected from the group consisting of interferons, immunoglobulins, lymphokines, growth factors, hormones, blood factors, and histocompatibility antigens.

11. The transgenic aloe cell of claim 1, wherein said exogenous protein is a mammalian protein selected from α-interferon, γ-interferon, prothrombin, dermicidin and human growth hormone.

* * * * *